United States Patent [19]

Martin

[11] Patent Number: 5,672,175

[45] Date of Patent: Sep. 30, 1997

[54] DYNAMIC IMPLANTED SPINAL ORTHOSIS AND OPERATIVE PROCEDURE FOR FITTING

[76] Inventor: Jean Raymond Martin, 11 rue des Sources, 31170 Tournefeuille, France

[21] Appl. No.: 595,421

[22] Filed: Feb. 5, 1996

Related U.S. Application Data

[63] Continuation of Ser. No. 196,319, Feb. 15, 1994, abandoned.

[51] Int. Cl.[6] .................................................. A61B 17/56
[52] U.S. Cl. ........................ 606/61; 606/90; 606/105; 606/60
[58] Field of Search ............................. 606/60, 61, 53, 606/57, 90, 105

[56] References Cited

U.S. PATENT DOCUMENTS

| | | | |
|---|---|---|---|
| 3,865,105 | 2/1975 | Lode | 606/61 |
| 3,977,397 | 8/1976 | Kalnberz et al. | |
| 4,078,559 | 3/1978 | Nissinen | 606/61 |
| 4,271,836 | 6/1981 | Bacal et al. | 606/61 |
| 4,289,123 | 9/1981 | Dunn | |
| 4,386,603 | 6/1983 | Matfield | |
| 4,445,513 | 5/1984 | Ulrich et al. | 606/105 |
| 4,448,191 | 5/1984 | Rodnyansky et al. | 606/61 |
| 4,573,456 | 3/1986 | Hoffman | |
| 4,611,582 | 9/1986 | Duff | |
| 4,836,196 | 6/1989 | Park et al. | |
| 4,854,496 | 8/1989 | Bugle | |
| 4,946,458 | 8/1990 | Harms et al. | 606/61 |
| 5,219,349 | 6/1993 | Krag et al. | 606/105 |
| 5,281,223 | 1/1994 | Ray | 606/61 |

FOREIGN PATENT DOCUMENTS

| | | | |
|---|---|---|---|
| 0 140 790 | 1/1984 | European Pat. Off. | |
| 0 140 790 | 5/1985 | European Pat. Off. | |
| 0 260 044 | 3/1988 | European Pat. Off. | |
| 0 470 660 | 2/1992 | European Pat. Off. | |
| 1 397 395 | 3/1965 | France | |
| 2689750 | 10/1993 | France | |
| 2 697 744 | 5/1994 | France | |
| 28 21 678 | 11/1979 | Germany | |
| 28 45 647 | 5/1980 | Germany | |
| 38 07 346 | 6/1989 | Germany | |
| 485739 | 12/1975 | U.S.S.R. | |
| 848009 | 10/1979 | U.S.S.R. | 606/61 |
| 888968 | 12/1981 | U.S.S.R. | 606/61 |
| 780 652 | 8/1957 | United Kingdom | |
| 2 162 065 | 1/1986 | United Kingdom | |
| 2 198 647 | 6/1988 | United Kingdom | |
| WO8504096 | 9/1985 | WIPO | |
| WO9002527 | 3/1990 | WIPO | |
| WO9213496 | 8/1992 | WIPO | |

*Primary Examiner*—Michael Buiz
*Assistant Examiner*—Mark S. Leonardo
*Attorney, Agent, or Firm*—Harold H. Dutton, Jr.

[57] ABSTRACT

A dynamic implanted spinal orthosis which preserves at least in part the natural physiological mobility of the vertebrae while effecting and maintaining a correction of the relative positions of the vertebrae without osteosynthesis, graft or fusion, comprising anchoring components fixed to the vertebrae and holding means associated with the anchoring components for holding the vertebrae with respect to each other in the corrected position, the holding means comprise an elastic return device for exerting elastic return forces, the orientation and magnitude of which are determined for holding the vertebrae in the corrected position against natural deforming forces for reducing the forces exerted on the vertebrae while preserving their mobility; also a procedure for maintaining a correction of the positions of the vertebrae for treating a deformation of the spine.

26 Claims, 10 Drawing Sheets

Fig 3
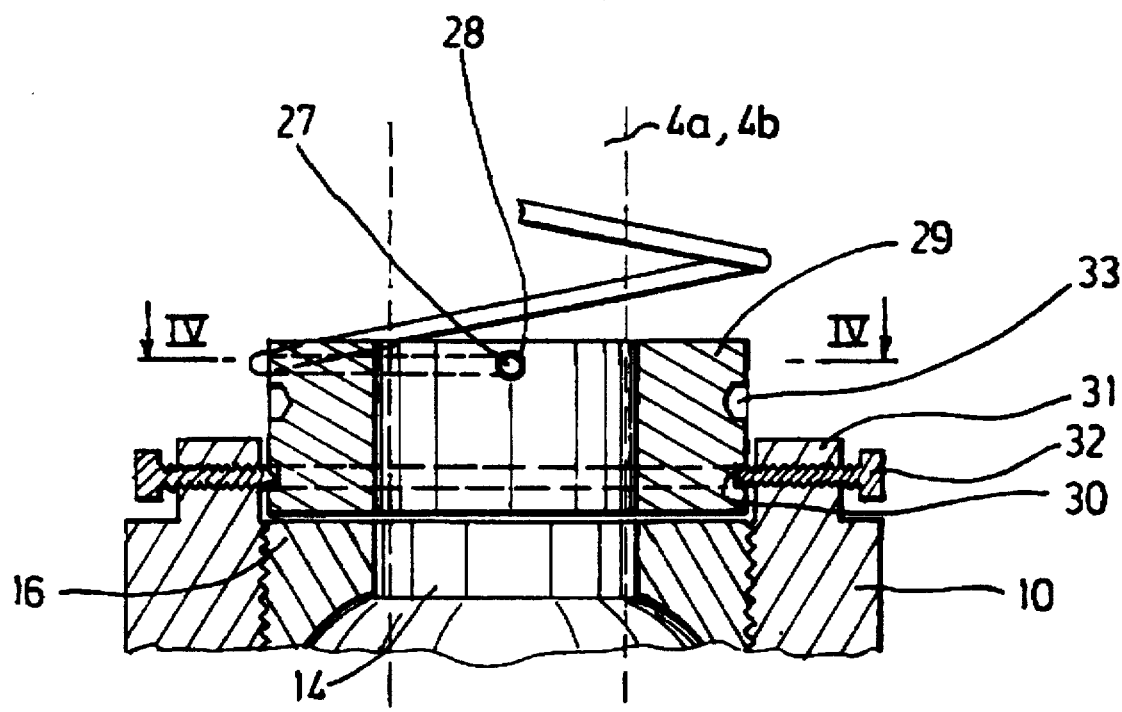
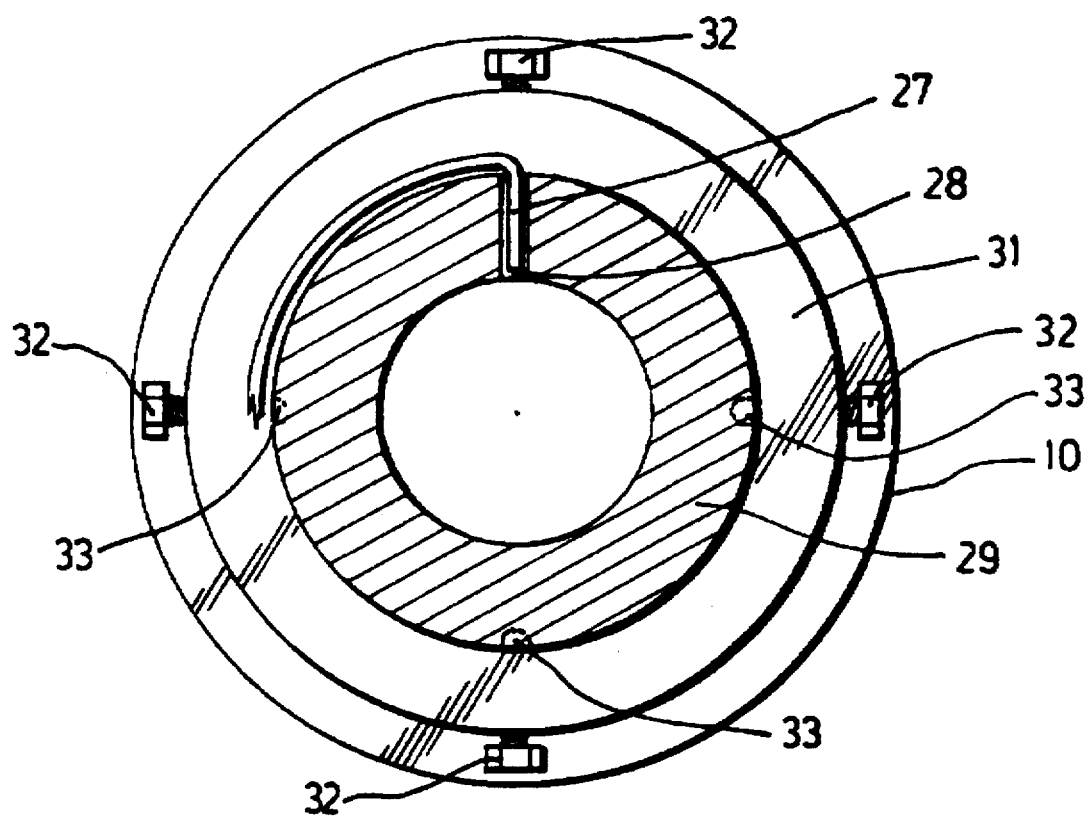
Fig 4

DYNAMIC IMPLANTED SPINAL ORTHOSIS AND OPERATIVE PROCEDURE FOR FITTING

This application is a continuation of Ser. No. 08/196,319, filed Feb. 15, 1994, now abandoned The present invention concerns a dynamic implanted spinal orthosis for effecting and maintaining a correction of the relative positions of the vertebrae and/or of the static and dynamic forces exerted on the vertebrae, for treating a congenital or acquired deformation of the spine, in particular an idiopathic condition such as kyphoscoliosis, or a post-traumatic, tumorous, infectious, degenerative or other, instability of the spine.

PRIOR ART

Spinal devices for reducing scoliotic deformations are already known, consisting of components for anchoring in the vertebrae, such as hooks or intrapedicular screws, and of rods or frames fixed to the anchoring components to impose a relative position on the various vertebrae. These rigid or semi-rigid osteosynthesis devices produce a rigidification of the spinal column in the corrected position and are always associated with a bone graft for spinal fusion. Consequently, the fitting of such an osteosynthesis device has the effect of permanently suppressing the natural physiological mobility of the vertebrae. Thus these known osteosynthesis devices, though they solve to a large extent the problems connected with scoliotic deformation, necessarily result in a handicap for the patient. This handicap is all the more serious because it is permanent and generally affects patients who are young and still growing. These devices constitute an obstacle to the subsequent growth of the spine.

Furthermore, the known osteosynthesis devices pose numerous further problems with regard to the positioning and reliability of the anchoring components, which are subjected to high stresses because of the subsequent rigidity, and at the time of the fixing of the rods, plates or frames to the anchoring components, which must be carried out at the same time as the reduction of the deformation. Various semi-rigid osteosynthesis devices have thus been proposed to resolve these drawbacks by preserving a certain elasticity which assists the fusion of the subsequent bone graft and facilitates the positioning of the anchoring components or reduces the stresses transmitted to the anchoring components. For example, FR-A-2 689 750 proposes such an osteosynthesis device in which the rods have a flexibility with a high elastic limit. The elasticity thus preserved in the area of the fusion assists the healing of the bone graft. Nevertheless, the problems connected with the rigidification of the column persist after this fusion. Similarly, U.S. Pat. No. 4,836,196 describes a spacing device disposed between anchoring components and a rigidification structure, making it possible to reduce the stresses transmitted between the vertebral body and the structure. Similarly, U.S. Pat. No. 4,573,454 describes a device with an extensible structure consisting of a frame in two parts, one of which telescopes into the other, for the purpose of assisting subsequent growth in spite of the rigidification of the spine. Nevertheless, this problem is only partially solved since the portions of the spine fixed respectively to each of the parts of the structure are themselves rigidified without growth being possible.

In addition, the reduction of the deformation at the time of the fitting of the osteosynthesis device poses further problems. This is because the reduction of the deformation should be able to be effected at the very same time as the fitting of the spinal appliance, and in all three dimensions. In particular, in the case of scoliosis, it is necessary not only to replace the vertebrae in the same sagittal plane but also to re-establish the kyphosis and/or lordosis while effecting a derotation of the vertebrae. The osteosynthesis devices of the Cotrel-Dubousset type make it possible to solve this problem partially. They consist of two posterior bilateral rods which are curved during the surgery, immediately before they are mixed in the anchoring components in accordance with the lateral deviation, and then rotated to place their curve in a sagittal plane in order to re-establish the kyphosis or lordosis at least partially and to effect a derotation of the vertebrae. The correction is limited by the fact that it is effected solely by the rod of the concavity which is rotated first. The rod placed in the convexity is modelled on the correction obtained and has only a stabilising effect when inserted. The two rods are then connected to each other by transverse traction devices stabilising the position of the whole. However, the curvature of the rods, which is essentially determined as a function of the lateral deviation to be corrected, does not necessarily correspond to an appropriate correction of the kyphosis or lordosis. In addition, these devices are considered to be among the most elaborate and the most rigid. As a result, fitting them is an extremely delicate surgery and the bone structure is sometimes too fragile to withstand the mechanical stresses generated. Whether these devices are rigid or semi-rigid, they are in all cases associated with a graft and therefore lead to the suppression of any movement: the result is a concentration of forces on the ends of the area to which the appliance has been fitted with a development of discoligamentary degeneration on these sites and/or excessive strain being placed on the joints.

In addition to the Cotrel-Dubousset devices, two other types of osteosynthesis devices are used to reduce the deformation of the spinal column. These are on the one hand Roy-Camille devices with plates and pedicular screws and improvements thereto, and on the other hand Luque devices with sub-laminar wires and improvements thereto. The Roy-Camille devices are restricted to low-amplitude corrections concerning a limited number of vertebrae and do not permit effective derotation. The Luque devices can give rise to serious neurological complications given that wires are passed under the vertebral laminae in the proximity of the spinal cord.

None of the known osteosynthesis devices enables a deformation to be corrected while preserving at least in part the natural physiological mobility of the vertebrae and subsequent possibilities for growth.

In addition, various elastic intervertebral devices for treating degenerative lumbar instabilities are also known. These devices generally consist of intervertebral ligaments or of springs (sometimes accompanied by bolsters) interposed between the spinous processes or between intrapedicular screws. These ligaments or springs exert traction forces tending to bring the vertebrae closer together and to reduce their relative mobility. These known devices therefore also considerably limit the natural physiological mobility of the vertebrae to which the appliance has been fitted. In addition, the elastic ligaments rapidly lose their mechanical qualities because they are subjected to very high stretching forces. Furthermore, these devices are unsuitable for correcting a deformation, in particular because of their excessive bending flexibility in the frontal plane. Also, after they have been fitted, it is not possible to vary the elasticity of the implanted devices.

The invention therefore aims to remedy the drawbacks of all the known devices by proposing a new dynamic implanted spinal orthosis, preserving at least in part the natural physiological mobility of the vertebrae and making it possible, without osteosynthesis or graft for fusion, to effect and maintain a correction of the relative positions of the vertebrae and/or to reduce the forces exerted on the vertebrae, for treating a congenital or acquired deformation of the spine, in particular an idiopathic condition such as kypho-scoliosis, or a post-traumatic, tumorous, infectious, degenerative or other instability of the spine. Thus the invention aims to propose a novel category of dynamic implanted spinal orthosis which, unlike known osteosynthesis devices, may be subsequently modified or even removed, and preserves the natural physiological mobility of the vertebrae not only when it is implanted but also after its subsequent removal.

The invention also provides a dynamic implanted spinal orthosis which preserves the growth potential of the spinal column. The invention also provides a dynamic implanted spinal orthosis which can subsequently be removed, in particular at the end of the period of growth when the risks of a worsening or recurrence of the deformation or instability have disappeared.

The invention also provides a dynamic implanted spinal orthosis which can be fitted with the minimum possible risk of affecting the nervous system.

The invention also aims to propose a dynamic implanted spinal orthosis transmitting to the anchoring components fixed to the vertebrae the lowest possible mechanical stresses, and in particular mechanical stresses of a magnitude which is strictly limited to that necessary for maintaining the correction of the deformation and/or applying the desired forces to the vertebrae.

The invention also provides a dynamic implanted spinal orthosis, the characteristics of which can be adjusted during fitting, and after implantation, by transcutaneous or percutaneous adjustments, as required.

More particularly, the invention provides a dynamic implanted spinal orthosis enabling the deformation of the spinal column to be reduced accurately in three dimensions.

The invention therefore provides a dynamic implanted spinal orthosis enabling scolioses to be reduced while preserving the natural physiological mobility of the vertebrae.

The invention also relates to a procedure for effecting and maintaining, without osteosynthesis or graft for fusion, a correction of the relative positions of the vertebrae and/or of the forces exerted on the vertebrae for treating a congenital or acquired deformation of the spine, in particular an idiopathic deformation such as kypho-scoliosis, or a post-traumatic, tumorous, infectious, degenerative or other, instability of the spine, preserving at least in part the natural physiological mobility of the vertebrae.

The invention provides a procedure for fitting and using a dynamic implanted spinal orthosis according to the invention.

SUMMARY OF THE INVENTION

For this purpose, the invention concerns a dynamic implanted spinal orthosis preserving at least in part the natural physiological mobility of the vertebrae while making it possible, without osteosynthesis or graft for fusion, to effect and maintain a correction of the relative positions of the vertebrae and/or of the forces exerted on the vertebrae, for treating a congenital or acquired deformation of the spine, in particular an idiopathic deformation such as kypho-scoliosis, or a post-traumatic, tumorous, infectious, degenerative or other, instability of the spine, comprising anchoring components fixed to the vertebrae and holding means associated with the anchoring components in order to hold the vertebrae with respect to each other in the corrected position in which the shape of the spinal column and/or the forces exerted on the vertebrae are corrected, characterised in that the holding means include or consist of elastic return means exerting elastic return forces, the orientation and magnitude of which are determined so as to hold the vertebrae in the corrected position against the natural deforming forces or so as to reduce the forces exerted on the vertebrae while preserving their mobility.

According to the invention, the orthosis includes at least one holding rod which is connected, so as to be movable, to the anchoring components for at least one vertebra by coupling means which prevent all relative sliding movement in horizontal translation, (ie in the lateral and anteroposterior directions with respect to the vertebra) but allow, after fitting, a relative movement in at least one other degree of freedom.

Thus the dynamic implanted spinal orthosis according to the invention is not an osteosynthesis device causing a rigidification of the spinal column. On the contrary, it constitutes a dynamic system generating forces which correct the vertebrae with respect to each other. The mobile connections produced by the coupling means allowing relative movements in at least one degree of freedom enable the natural physiological mobility of the vertebrae with respect to each other to be preserved. The only sources of rigidity resulting from the orthosis according to the invention are those which are necessary to effect and maintain a correction of the relative positions of the vertebrae. It has in fact been established that these limitations on mobility are indeed necessary and sufficient to treat the majority of deformations and instabilities. Moreover, the orthosis according to the invention is fitted without a bone graft.

The number, nature, orientation and magnitude of the elastic return forces and of the degrees of freedom allowed by the means of coupling the holding rods to the anchoring components are determined in accordance with the degree and rigidity of the spinal deformation or instability.

Advantageously and according to the invention, each holding rod is connected to the anchoring components for one vertebra by coupling means preventing all relative movement between the holding rod and the anchoring components. Moreover, the means of coupling this holding rod to all the anchoring components for the other vertebrae allow, after fitting, a relative movement according to at least one degree of freedom.

In the case of a correction of a lateral deviation of the spinal column (scoliosis), the holding rods are preferably connected rigidly with a middle vertebra by coupling means preventing all relative movement, and connected so as to be able to move in at least one degree of freedom with respect to the anchoring components for the other vertebrae, in particular the vertebrae at the end of the deformation to be corrected.

According to the invention, the degree of freedom allowed by the means of coupling the holding rods to the anchoring components may be a relative longitudinal translation along a vertical axis and/or a relative rotation about an axis perpendicular to a frontal plane and/or a relative rotation about a vertical axis and/or a relative rotation about an axis perpendicular to a sagittal plane. In particular, rotations about any horizontal axis are allowed.

For example, according to the invention, in the case of the treatment of lumbar instability, the degrees of freedom allowed may be a relative longitudinal translation along a vertical axis, a relative rotation about an axis perpendicular to a frontal plane and a relative rotation about a vertical axis. In the case of the treatment of scoliosis, a relative rotation about an axis perpendicular to a sagittal plane is also provided for. Thus, in the latter case, any rotation about a horizontal axis is allowed. According to the invention, these degrees of freedom are provided for in the case of all means of coupling the holding rods to the anchoring components for all the vertebrae fitted with the appliance, with only one exception.

According to the invention, the elastic return means are connected with the anchoring components for the vertebrae with a shape that is different from their shape when idle, that is to say their shape before they are fitted, so as to exert forces when the vertebrae are in the corrected position and in order to maintain this position.

According to the invention, the holding means include at least one curved holding rod which is flexible and elastic in bending connected with anchoring components for at least two different vertebrae and able, after fitting, to exert elastic forces for holding the vertebrae in the corrected position while allowing physiological movements from the corrected position of the vertebrae. Moreover, the means of coupling this rod to the anchoring components for at least one vertebra include a cylindrical bore through which the rod passes and in which it can slide in translation.

According to the invention, this bore is formed in a member mounted so as to rotate with respect to the anchoring components about an axis perpendicular to the frontal plane and/or about an axis perpendicular to the sagittal plane of the corresponding vertebra. This member may be a sphere with a cylindrical bore, and this sphere is enclosed in a spherical housing fixed to the anchoring components allowing it complete freedom of rotation about all the axes situated in the horizontal plane. Furthermore, according to the invention, the means of coupling the rod to the anchoring components for at least one vertebra allow rotation of the rod itself about its axis with respect to the anchoring components.

According to the invention, each rod is placed in a lateral position with respect to the spinous process in the paravertebral grooves.

The orthosis according to the invention may comprise a single rod on one side of the spinous process or two rods, one on each side. Each of the rods is curved initially during manufacture, so that its neutral position is arched. When fitted and connected to the anchoring components, the curvature of each of the rods is modified so that it exerts elastic bending stresses on the anchoring components. The material and dimensions of each rod are determined so that subsequent intentional elastic bending movements of the spinal column are possible, after fitting and from the corrected position of the vertebrae.

Advantageously and according to the invention, the holding means include at least one spring acting on the anchoring components for at least one vertebra. Such a spring may be a spring with contiguous or non-contiguous coils, one end of which is associated with the anchoring components for one vertebra and the other end of which is associated with anchoring components for another vertebra. Such a coil spring may be a compression or extension spring surrounding a holding rod connecting the anchoring components for the different vertebrae to which the device is fitted. The rod then acts as a guide for the spring. Thus, according to the invention, the holding means include, on the concave side of a deformation to be corrected and/or on the convex side of a deformation to be corrected, a rod and at least one compression and/or extension spring surrounding the rod. According to the invention, the two ends of a spring can be locked to the anchoring components for two vertebrae—and in particular the central vertebra—with respect to rotation so as to communicate a torsional moment to these vertebrae. To this end, the coils of the spring are wound or unwound compared with their shape when idle after the association and before the fixing of the ends of this spring to the anchoring components. Such a torsional moment communicated by a spring surrounding a rod makes it possible to exert a turning moment of the vertebrae with respect to each other.

An orthosis according to the invention has in addition means for adjusting the magnitude of the elastic return forces exerted at least by part of the elastic return means.

According to the invention, adjustment means make it possible to vary, in the corrected position of the vertebrae, the elastic elongation (ie the elastic variation in length or shape) of the elastic return means with respect to their shape when idle. These adjustment means may consist of at least one electronic micromotor and/or at least one manual device for adjusting the position of a stop for the elastic return means with respect to anchoring components for one vertebra. According to the invention, the adjustment means comprise means of transcutaneous or percutaneous control after the implantation of the orthosis, in the form, for example, of an electromagnetic control.

According to the invention the adjustment means include at least a part of the holding means and/or elastic return means which is formed from a shape-memory metal alloy. Consequently, the adjustment can be carried out by heating this part so as to restore its shape entirely or partly in order to use its elasticity as required. Thus the rods and/or springs can be formed wholly or partly from a shape-memory metal alloy.

The invention also concerns a procedure for effecting and maintaining, without osteosynthesis or graft for fusion, a correction of the relative positions of the vertebrae and/or of the forces exerted on the vertebrae for treating a congenital or acquired deformation of the spine, in particular an idiopathic deformation such as kyphoscoliosis, or a post-traumatic, tumorous, infectious, degenerative or other instability of the spine, preserving at least in part the natural physiological mobility of the vertebrae, in which anchoring components are fixed to the vertebrae, and holding means are associated with the anchoring components in order to hold the vertebrae with respect to each other in the corrected position in which the shape of the spinal column and/or the forces exerted between the vertebrae are corrected, wherein:

the vertebrae intended to receive anchoring components are exposed, the anchoring components are fitted and fixed to each vertebra concerned, operative instrumentation is associated with the anchoring components for each vertebra to be moved for the required correction, the operative instrumentation is operated in order to place the vertebrae in the corrected position (ie with a corrected shape of the spinal column and/or static intervertebral forces reduced according to the desired value), the necessary holding forces applied to the anchoring components for each vertebra in order to maintain the corrected position are measured, the characteristics of the holding means, notably of elastic return means for these holding means for the orthosis, are determined so as to generate elastic return forces similar to the holding forces measured, the holding means and the elastic return means are associated with the anchoring components for each vertebra, the operative instrumentation is removed, the surgical implantation procedure is completed.

According to the invention, the holding forces are measured by dynamometric sensors fixed to the operative instrumentation along three orthogonal translational axes of the operative instrumentation. In addition, the characteristics of the holding means and elastic return means are determined by computation by means of a data processing device using the values of the holding forces in the corrected position as measured by dynamometric sensors. These characteristics are also checked a posteriori by checking that the values measured by the dynamometric sensors are cancelled out after the fitting of the holding means and elastic return means. Failing this, the holding means and elastic return means can be changed by using devices with more appropriate characteristics.

According to the invention, after removing the operative instrumentation, the maintenance of the said corrected position is checked and the necessary adjustments to the elastic return means are carried out by acting on the means of adjusting these elastic return means. It is thus possible to act on the adjustment means during the surgical operation or even after the implantation of the orthosis and when the patient is awake after the surgery.

According to the invention, an operative clamp is associated with the components for anchoring any one side of the spinous process, and in particular a first operative clamp with the components for anchoring one side of the spinous process and a second operative clamp with the components for anchoring the other side of the spinous processes.

The invention also concerns a dynamic implanted spinal orthosis and a procedure for fitting such an orthosis including in combination all or some of the characteristics mentioned above or below.

DESCRIPTION OF THE FIGURES

Other characteristics, aims and advantages of the invention will become clear through a reading of the following description of these preferred embodiments which refer to the accompanying drawings, in which:

FIG. 3 is a diagrammatic view in vertical section and in detail of means of locking with respect to rotation one end of a spring of an orthosis according to the invention, FIG. 4 is a diagrammatic view in cross section along the line IV—IV in FIG. 3.

DETAILED DESCRIPTION

Throughout the text, and except where otherwise indicated, the term "vertical" designates the axial direction of the spinal column, which does not correspond to the absolute vertical direction since the spinal column is curved (kyphosis and lordosis). Similarly the term "horizontal" designates any direction contained in the plane at right angle to the vertical direction, the term "sagittal" designates any plane containing the anteroposterior vertical and horizontal directions, and the term "frontal" designates any plane containing the lateral vertical and horizontal directions. These terms are thus used with reference to each vertebra.

Figure 1:
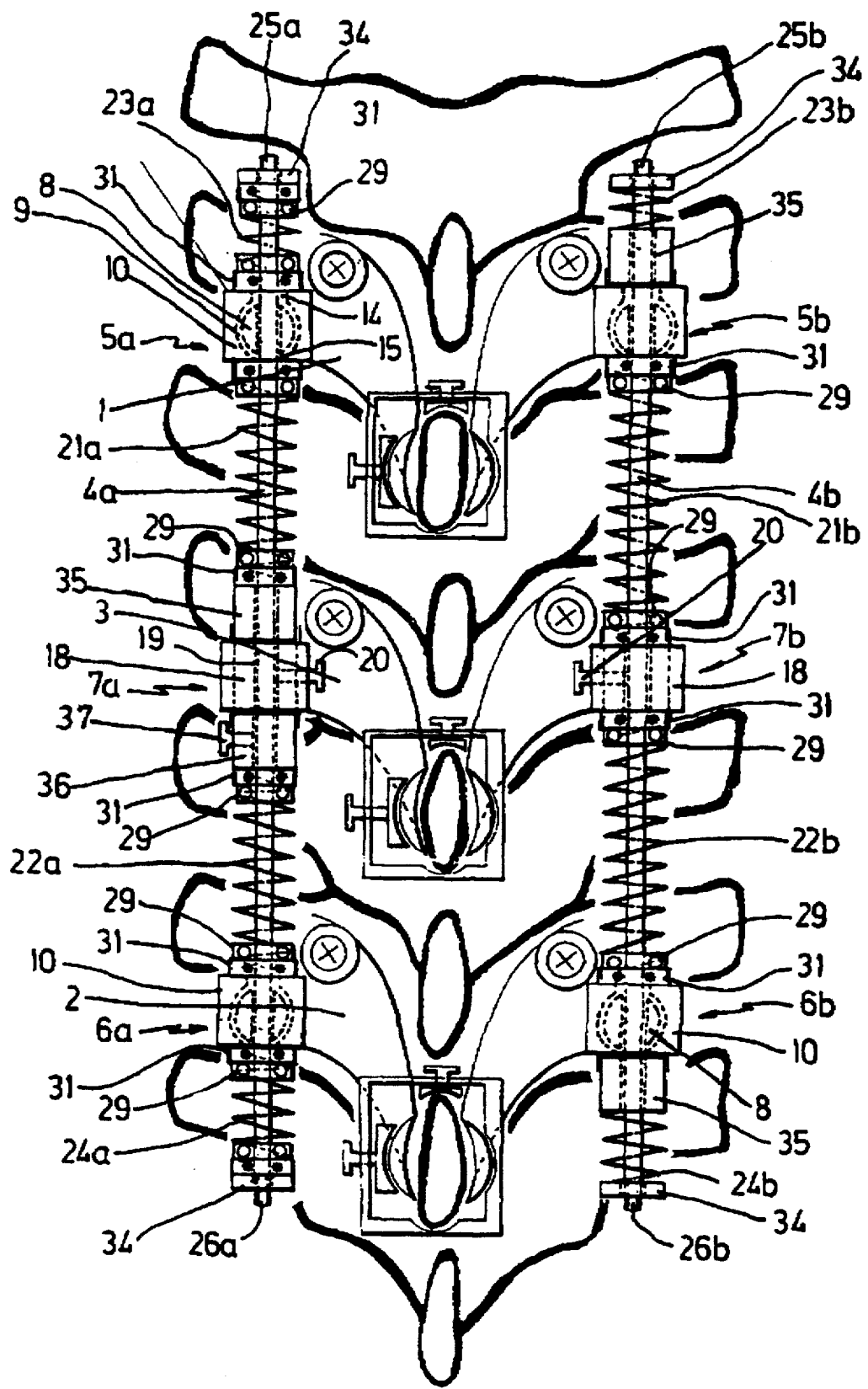
FIG. 1 is a posterior diagrammatic view of a first embodiment of an orthosis according to the invention, more particularly designed for the treatment of scoliosis.
Figure 11:
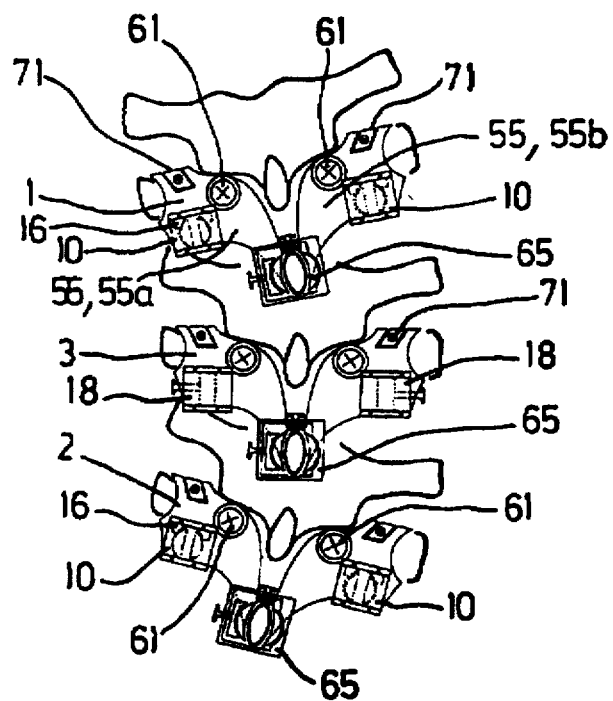
FIG. 11 is a posterior diagrammatic view illustrating a first stage of fitting the orthosis in FIG. 1.

FIG. 1 shows a first embodiment of a dynamic implanted spinal orthosis according to the invention which enables a correction of the relative positions of five dorsal vertebrae to be effected and maintained for treating a deformation of the scoliotic type. Before the fitting of the orthosis, the vertebrae exhibit a lateral deviation such as a curvature, the convexity of which is oriented towards the right (FIG. 11). The orthosis according to the invention comprises an anchoring component 1 fixed to the topmost vertebra, an anchoring component 2 fixed to the lowest vertebra, and an anchoring component 3 fixed to the middle vertebra located in the centre of the natural original curvature of the scoliosis.

The orthosis also includes two holding rods 4a, 4b extending laterally on each side of the spinous processes, ie a left-hand rod 4a placed on the same side as the concavity of the deformation to be corrected and a right-hand rod 4b placed on the same side as the convexity of the deformation to be corrected. Each rod 4a, 4b is a curved flexible rod, elastic in bending, made of biocompatible material such as a metal alloy (stainless steel or titanium) and/or a composite material. Each rod 4a, 4b is connected to components 1, 2, 3 for anchoring the vertebrae using coupling means 5a, 5b, 6a, 6b, 7a, 7b. Each rod 4a, 4b is curved initially during manufacturing and is connected to the anchoring components, extending in a sagittal plane with its convexity oriented in the posterior direction. This initial curvature of the rods 4a, 4b is not modified before they are fitted. The rods 4a, 4b are made of a material with high breaking strength and with a high modulus of elasticity. Their dimensional and mechanical characteristics are determined in such a way that these rods 4a, 4b are able, after being fitted, to exert elastic forces making it possible to maintain the vertebrae in the corrected position shown in FIG. 1, while allowing physiological movements from this corrected position of the vertebrae. In order to exert elastic return forces, the rods 4a, 4b have, once they are connected to the anchoring components 1, 2, 3 and are in the corrected position of the vertebrae, a shape which is different from their shape when idle. In particular, in the case of the correction of dorsal scoliosis, the curvature of the rods 4a, 4b when idle has a smaller radius than the curvature which they have when connected to the anchoring elements 1, 2, 3. In this way, the rods 4a, 4b exert, when in the corrected position of the vertebrae, elastic bending forces. These elastic bending forces also maintain the derotation of the vertebrae with respect to each other. The rods 4a, 4b therefore themselves constitute elastic return means exerting elastic return forces which are determined so as to maintain the vertebrae in the corrected position in opposition to the natural deformation forces. In addition, the dimensional and mechanical characteristics of the rods 4a, 4b are determined in such a way that these rods 4a, 4b have a residual elasticity from the corrected position of the vertebrae. In this way, the rods 4a, 4b do not oppose the natural physiological movements of the vertebrae with respect to each other from the corrected position. These physiological movements are also made possible by the coupling means 5a, 5b, 6a, 6b, 7a, 7b which are designed for this purpose.

The means 5a of coupling the left-hand rod 4a to the top anchoring component 1 for the top vertebra fitted with the appliance include a sphere 8 mounted so as to rotate freely and enclosed in a spherical housing 9 in a cylinder 10 fixed to the anchoring component 1 so as to form a connecting pivot. The sphere 8 has in it a cylindrical bore 11 through which the rod 4a passes and in which this rod 4a can slide in longitudinal axial translation in the vertical direction. The width of the bore 11 corresponds with the width of the rod 4a and the sphere 8 is engaged in the housing 9 without there being any possibility of relative horizontal translational movements, and in particular in the lateral and anteroposterior directions of the vertebra. In this way, the coupling means 5a thus produced prevent, after the fitting of the rod 4a, any relative horizontal translational movement of the rod 4a with respect to the anchoring components I and to the corresponding vertebra. On the other hand, these coupling means 5a allow, after the fitting of the rod, a relative movement in four other degrees of freedom: a relative longitudinal translational sliding along a vertical axis of the rod 4a and three degrees of freedom of rotation of the sphere 8 with respect to the cylinder 10, iea relative rotation about an axis perpendicular to a frontal plane, a relative rotation about an axis perpendicular to a sagittal plane and a relative rotation about a vertical axis. The bore 11 is cylindrical and the rod 4a has ribs 12 evenly distributed around its axis and extending along the rod 4a, projecting with respect to its outer face to come into contact along the inner face 13 of the bore 11. In the example shown, three ribs 12 have been given a triangular cross section. In this way contact friction is reduced. The materials forming the sphere 8 and cylinder 10 are chosen so as to allow rotations of this sphere 8 in the housing 9 as indicated above. For example, the sphere 8 is made from a metal alloy of high surface quality or from ceramic material and the cylinder 10 is made from a block of synthetic material such as high molecular weight polyethylene or the like. The sphere 8 and/or the cylinder 10 may be made from a self-lubricating material or have a coating made of this material.

The cylinder 10 has top 14 and bottom 15 openings enabling the rod 4a to pass through and whose widths are greater than those of the rod 4a to allow tilting movements of the rod 4a with respect to the axis of the cylinder under the effect of the above-mentioned rotational movements. Preferably, the dimensions of the openings 14 and 15 are such that they allow an amplitude of tilting of the rod 4a of at least 45° with respect to the vertical axis of the cylinder 10.

The sphere 8 is engaged in the spherical housing 9 when the rod 4a is fitted. In order to achieve this, a threaded ring 16 is mounted at the top (or bottom) end of the cylinder 10, which has a housing for receiving this ring 16 with a corresponding internal thread. The ring 16 has an axial bore which determines the top (or bottom) opening 14 of the cylinder 10 opening out into the spherical housing 9. The dimensions of the housing for receiving the ring 16 are defined so as to enable the sphere 8 to be inserted from the top (or bottom) into the spherical housing 9. The bottom (or top) face of the ring 16 has a concave shape like that of a portion of a sphere so that it extends the spherical inner face of the housing 9, enclosing the sphere 8 in this housing 9 (FIG. 3) without locking it. In a variant (FIG. 1), the cylinder is formed from a block of synthetic material and the top (or bottom) opening 14 has a diameter slightly less than that of the sphere 8, which may be forcibly engaged in the housing 9 through this opening 14, which then holds the sphere 8 in the housing 9.

Figure 15:
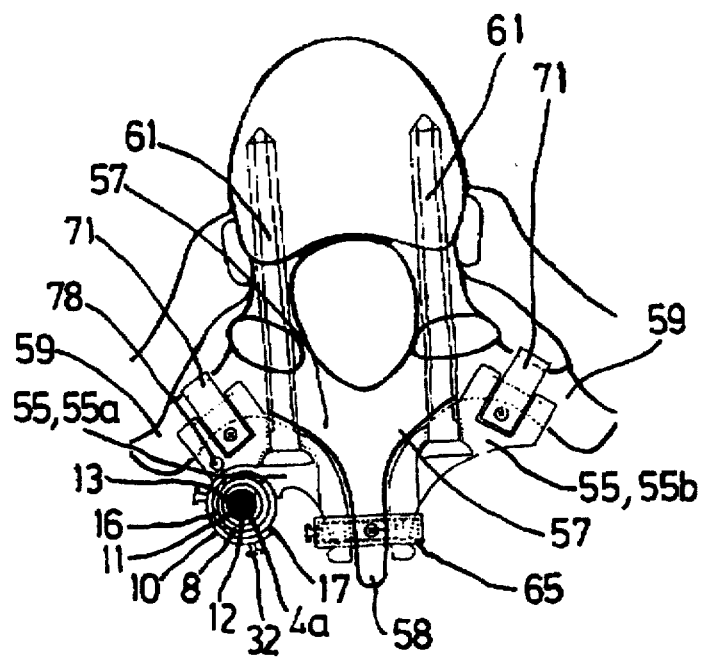
FIG. 15 is a diagrammatic view in cross section through a horizontal plane of the vertebra-anchoring components of an orthosis according to a fifth embodiment of the invention.

Before inserting the sphere 8 into the housing 9, the rod 4a is inserted inside the cylinder 10. To achieve this, this cylinder 10 has a slot 17 extending from top to bottom, communicating with the housing 9, and the width of which corresponds to the largest diameter envisaged for the rod 4a. This slot 17 may be placed on the inside of the cylinder 10 opposite the spinous processes, as shown in FIG. 15, or on the opposite side, or even on the posterior side. However, this slot 17 is preferably formed in a portion of the cylinder 10 which is subject to the least stress in the horizontal radial direction. In order to mount the assembly, the sphere 8 is engaged around the rod 4a by inserting this rod 4a through the bore 11, the rod 4a is inserted into the housing 9 through the slot 17 while keeping the sphere 8 above (or below) the cylinder 10, and then the sphere 8 is engaged in the housing 9. In the embodiment shown in FIG. 3, the ring 16 is then screwed into the corresponding housing in the cylinder 10. If necessary, this ring 16 will have been engaged beforehand around the rod 4a above the sphere 8. The diameter of the rods 4a, 4b, which can be adapted to the same anchoring components, may thus vary, the adaptation being achieved by using spheres 8, the bore 11 of which corresponds to the diameter of the rods 4a, 4b.

The means 6a for coupling the rod 4a with respect to the bottom anchoring component 2 for the lowest vertebra are identical to the previously described means 5a for coupling this rod 4a to the top anchoring component 1 for the topmost vertebra. On the other hand, the means 7a for coupling the rod 4a to the middle anchoring component for the middle vertebra are rigid connection means preventing all relative movement of the rod 4a with respect to the anchoring component 3. To achieve this, these coupling means 7a consist of a cylinder 18 mounted so as to be fixed to the anchoring component 3 and having a cylindrical bore 19 extending from top to bottom and through which the rod 4a passes. This bore 19 is similar to the bore 11 in the coupling means 5a previously described, and therefore has the shape and dimensions corresponding to those of the rod 4a. In a variant which is not shown, the bore 19 may be produced in an adapting cylinder, the internal diameter of which may vary and which is mounted so as to be concentric in the cylinder 18. In addition, the cylinder 18 carries one or more screws 20 for the transverse locking of the rod 4a. The screw 20 is engaged in a corresponding internal thread in the cylinder 18 which opens out into the bore 19. By tightening the screw 20, the latter bears on the rod 4a and locks it to the bore 19 with respect to translational movement. In order to assist this locking, the rod 4a may have one or more horizontal peripheral grooves. In addition, the cylinder 18 has a slot from top to bottom for the mounting of the rod 4a in the bore 19.

Thus the rod 4a is locked by the coupling means 7a with respect to the anchoring component for the middle vertebra in each degree of freedom for which the rod 4a is associated so as to be movable with respect to the anchoring components 1, 2 for the other vertebrae. This is because it is important that the rod 4a should be locked by coupling means with respect to the anchoring components for at least one vertebra in at least one—notably each—degree of freedom for which this rod 4a is associated so as to be movable by coupling means with respect to the anchoring components for at least one other vertebra. However, the locking of the rod 4a in the different degrees of freedom may not be combined on the same vertebra. In some cases also, the rod 4a can be locked in one or more degrees of freedom with respect to several distinct vertebrae. In most cases, nevertheless, it is advantageous to provide for the rod 4a to be locked in all the degrees of freedom with respect to the anchoring components 3 for one and the same vertebra and associated so as to be movable in the different degrees of freedom provided for with respect to all the anchoring components 1, 2 for the other vertebrae. Thus the rod 4a is locked by coupling means with respect to the anchoring components 3 for one of the vertebrae and associated so as to be movable by coupling means with all the anchoring components 1, 2 for the other vertebrae which allow, after fitting, a relative movement in at least one degree of freedom.

The rod 4b placed to the right of the spinous processes (FIG. 1) is associated with the anchoring components 1, 2, 3 by coupling means 5b, 6b, 7b similar to the coupling means 5a, 6a, 7a previously described for the left-hand rod 4a. In particular, the right-hand rod 4b is fixed rigidly to the same vertebra as the left-hand rod 4a, ie to the middle vertebra.

Each rod 4a, 4b thus mounted on the anchoring components 1, 2, 3 for the vertebrae forms a means of frontal and sagittal holding of the vertebrae with respect to each other. It also forms, to a certain extent, a means for holding the vertebrae in the vertical direction. Once fitted, these rods 4a, 4b exert elastic return forces on the anchoring components in opposition to the natural deformation forces. The corrected position in fact corresponds to the position of equilibrium between the natural deformation forces of the spinal column and the elastic return forces exerted by the orthosis according to the invention. Given the flexibility of the rods 4a, 4b and the degrees of freedom allowed by the various coupling means, natural physiological movements are possible at least to a certain extent with respect to the corrected position.

In most cases, the bending elasticity of the rods 4a, 4b will on its own be considered to be inadequate to effect and maintain the deformation correction given the forces involved, the spatial constraints and the flexibility which these rods must have to allow movements. According to the invention, the elastic return means of the orthosis include at least one spring 21a, 21b, 22a, 22b, 23a, 23b, 24a, 24b acting on the anchoring components for at least one vertebra. In the embodiment in FIG. 1, the orthosis has for each rod 4a, 4b a coil spring 21a, 21b interposed between the anchoring components 1, 3 for the top vertebra and the middle vertebra, a coil spring 22a, 22b interposed between the anchoring components 2, 3 for the bottom vertebra and the middle vertebra, a coil spring 23a, 23b interposed between the anchoring component 1 for the top vertebra and a free top end 25a, 25b of the rod 4a, 4b, and a coil spring 24a, 24b interposed between the anchoring component 2 for the bottom vertebra and the free bottom end 26a, 26b of the rod 4a, 4b. Each coil spring 21a, 21b, 22a, 22b is interposed between the anchoring components 1, 3 and 3, 2 for two different vertebrae and has one end connected to the anchoring component 1 or 3 for one vertebra and the other end connected to the anchoring component 3 or 2 for another vertebra. The springs 21a, 22a, 23b, 24b are compression springs. The springs 21b, 22b, 23a, 24a are extension springs.

The ends of the springs 21a, 23a acting on the anchoring component 1 and placed around the left-hand rod 4a, bear on the cylinder 10. The ends of the springs are mounted with respect to the anchoring component 1 so as to communicate a torsional moment to the corresponding vertebra. To achieve this, the free end 27 of the spring which is bent so as to extend radially and inwardly is inserted into a radial drilling 28 in a ring 29. In a variant, the last coil of the spring is welded to the ring 29. This ring 29 has an external circumferential groove 30. The cylinders 10 have an outer collar 31 surrounding the ring 29. This collar 31 carries radial locking screws 32 engaged in internal screw threads in the collar 31 and the ends of which enter the groove 30 in the ring 29 so as to lock it axially with respect to the cylinder 10 and then, after torsion of the spring, to lock it to the cylinder 10 with respect to rotation. The ring 29 has blind holes 33 enabling it to be caused to rotate about the axis of the spring. When the desired torsion is obtained, the screws 32 are finally tightened so as to lock the ring 29 with respect to the collar 31 of the cylinder 10. Such a ring 29 locked by screws 32 may be provided not only at each end of its spring bearing on anchoring components including a cylinder 10 or 18, but also at the end of a spring bearing on a nut 34 fixed at the end 25a, 25b, 26a, 26b of a rod 4a, 4b.

Figure 7:
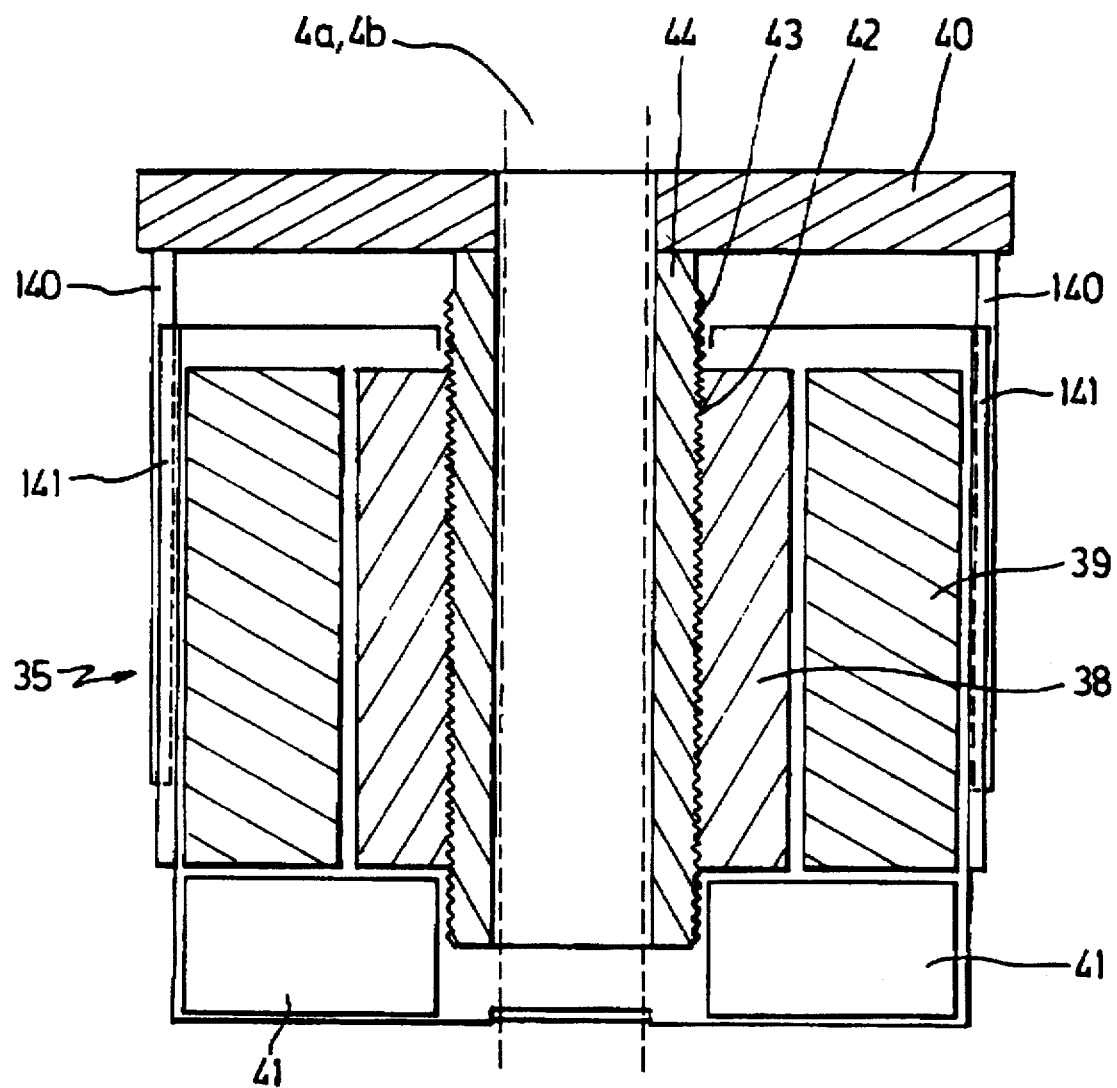
FIG. 7 is a diagrammatic view in vertical section and in detail of a micromotor for adjusting the elastic return means of an orthosis according to the invention.

According to the invention, the orthosis also includes means 35, 36 for adjusting the magnitude of the elastic return forces exerted by at least some of the elastic return means, ie the rods 4a, 4b and/or the springs. These means 35, 36 are means for varying, in the corrected position of the vertebrae, the initial elastic elongation (ie the initial elastic variation, in compression or traction, of length or shape) of the elastic return means with respect to their shape when idle. This is because both the rods 4a, 4b and the springs are fitted and connected to the anchoring components 1, 2, 3 in a shape which is different from their shape when idle so as to exert elastic forces in opposition to the natural deformation forces, and maintain the vertebrae in the corrected relative positions with respect to each other. However, the return forces exerted by the elastic return means vary with the said elastic elongation of these elastic return means with respect to their shape when idle. Consequently, by modifying this elastic elongation, the magnitude of the elastic return forces exerted is modified. In particular, the length of the compression and extension springs is decreased or increased. To achieve this, the said adjustment means may consist of a variable-height bolster interposed between one of the ends of the spring which it is desired to be able to adjust, and the corresponding support component, ie a cylinder 10 or 18 or a nut 34 at the end of the rod. Such a variable-height bolster 35, 36 may consist of an electronic micromotor 35 (FIG. 7) with a height of 1 to 2 centimeters and having a rotor 38 with an axial drilling.

The rotor 38 has an internal screw thread 42 which cooperates with the external screw thread 43 of an internal cylinder 44 carrying a movable plate 40. The plate 40 is locked, with respect to rotation, to the stator 39 of the micromotor by vertical rails 140 fixed to the plate 40 sliding in externals vertical channels 141 fixed to the stator 39.

When the micromotor 35 is operated, the plate 40, which bears on the end of the spring, slides in axial translation with respect to the stator 39 of the micromotor which bears on the cylinder 10 or 18 or on the corresponding nut 34. The stator 39 of the micromotor 35 may be mounted on the cylinder 10 or 18 or the corresponding nut 34 in the same way as the previously-described ring 29 for adjusting the torsion of the springs. For this purpose, the stator of the micromotor 35 has a circular peripheral groove in which radial locking screws such as 32 are tightened. Equally, the end of the spring bearing on the plate 40 of the micromotor 35 may be fixed to this plate 40 by torsion-adjustment means such as those described above, ie a ring 29 on which the end of the spring is mounted, which is itself mounted on a collar 31 on the plate 40 of the micromotor 35 by means of locking screws 32. The micromotor may be supplied with electrical energy by microbatteries 41, and its operation may be controlled through the skin by means of an electromagnetic or other remote-control device.

Figure 5:
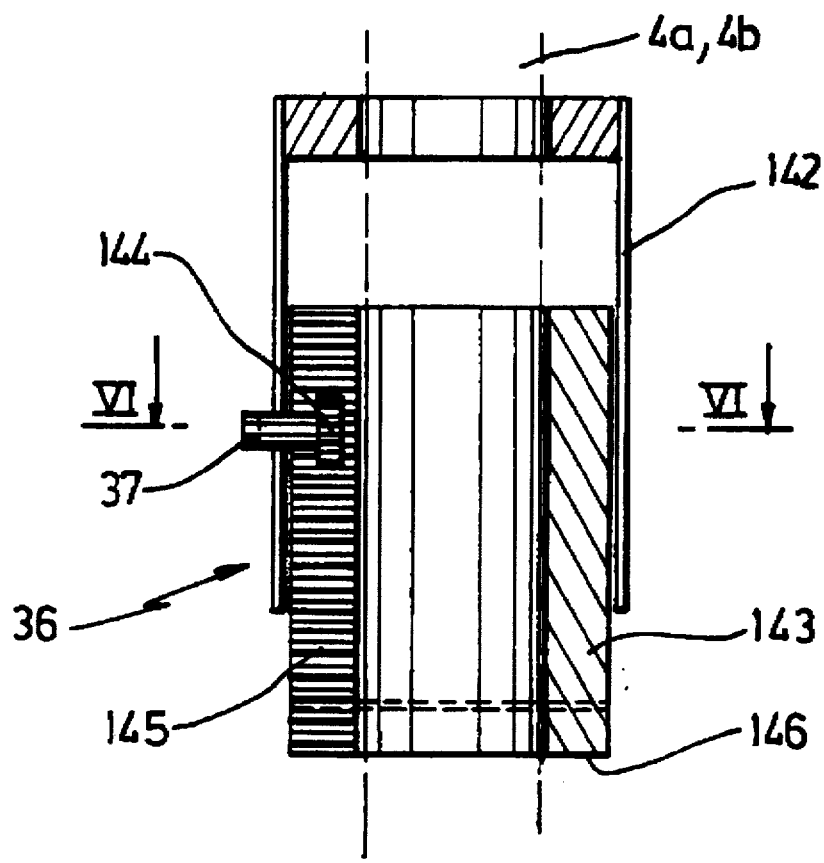
FIG. 5 is a diagrammatic view in vertical cross section and in detail of a device for manually adjusting the elastic return means of an orthosis according to the invention.
Figure 6:
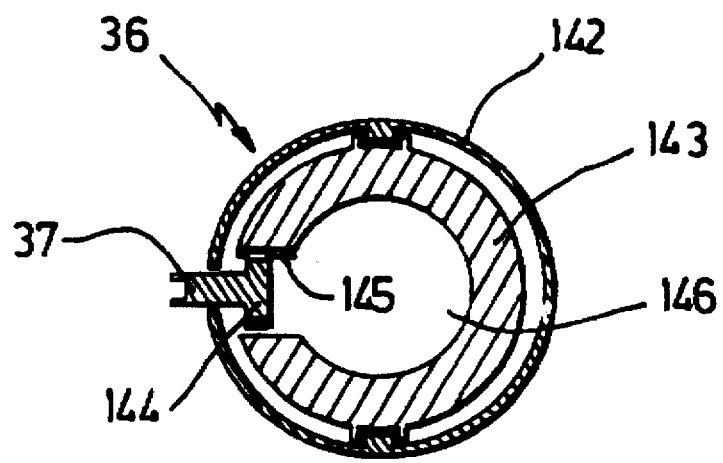
FIG. 6 is a diagrammatic view in cross section along the line VI—VI in FIG. 5.

As a variant or in combination, an adjustment bolster can consist of a manual adjustment device 36 (FIGS. 5 and 6) having two concentric cylinders 142, 143, one of which 143 is movable in vertical axial translation with respect to the other 142 which is fixed, under the action of a control screw 37 which extends radially and which carries, at its inner end, a pinion 144 cooperating with a rack 145 fixed to the movable cylinder 143 to actuate it in relative axial translation in one direction or the other. The cylinders 142, 143 are locked to each other with respect to rotation. The manual adjustment device 36 also comprises an axial central drilling 146 to enable the rod 4a or 4b to pass through the movable cylinder 143. It is interposed between one spring end and a cylinder 10, 18 or one rod-end nut 34. The manual adjustment device 36 may be fixed to the end of the spring and to the cylinder 10 or 18 or to the nut 34 in the same way as the micromotor 35, in particular through means of adjusting the torsion of the spring. By turning the screw 37, for example by percutaneous means, the movable cylinder 143 is caused to slide axially with respect to the fixed cylinder 142.

In the embodiment in FIG. 1, all the springs 21a, 22a, 23a, 24a surrounding the left-hand rod 4a are equipped with adjustment and torsion-locking means (ring 29 and locking screw 32). The two compression springs 21a, 22a bearing, on each side, on the cylinder 18 of the means 7a for coupling the rod 4a to the middle anchoring component 3, are provided with adjustment means 35, 36. An electronic micromotor 35 is shown above the cylinder 18 for adjusting the top spring 21a, and a manual tensioning device 36 with its screw 37 is shown below the cylinder 18 for adjusting the length of the bottom spring 22a.

The traction springs 21b, 22b interposed between the anchoring components around the right-hand rod 4b are also provided with adjustment and torsion-locking means 29, 32. Micromotors 35 for adjustment are provided between the cylinders 10 of the means 5b, 6b for coupling the rod 4b to the top and bottom anchoring components 1, 2, and the corresponding ends of the end springs 23b, 24b.

The adjustment of the return forces exerted by the springs which may be effected by means of the rings 29, micromotors 35 and manual tensioning devices 36 makes it possible to adapt the characteristics of the orthosis easily in accordance with the natural physiological changes in the patient (increase in the length of the spinal column, the weight of the body, the strength of the muscles, etc). Nevertheless, if these physiological changes are too great, the adjustment may prove to be inadequate. In such case, the rods 4a, 4b and/or the springs can still be changed easily. The anchoring components 1, 2, 3 do not generally need to be modified, since the coupling means 5a, 5b, 6a, 6b, 7a, 7b allow the mounting and removal of the rods and springs with respect to these anchoring components in the course of an operative procedure.

Figure 2:
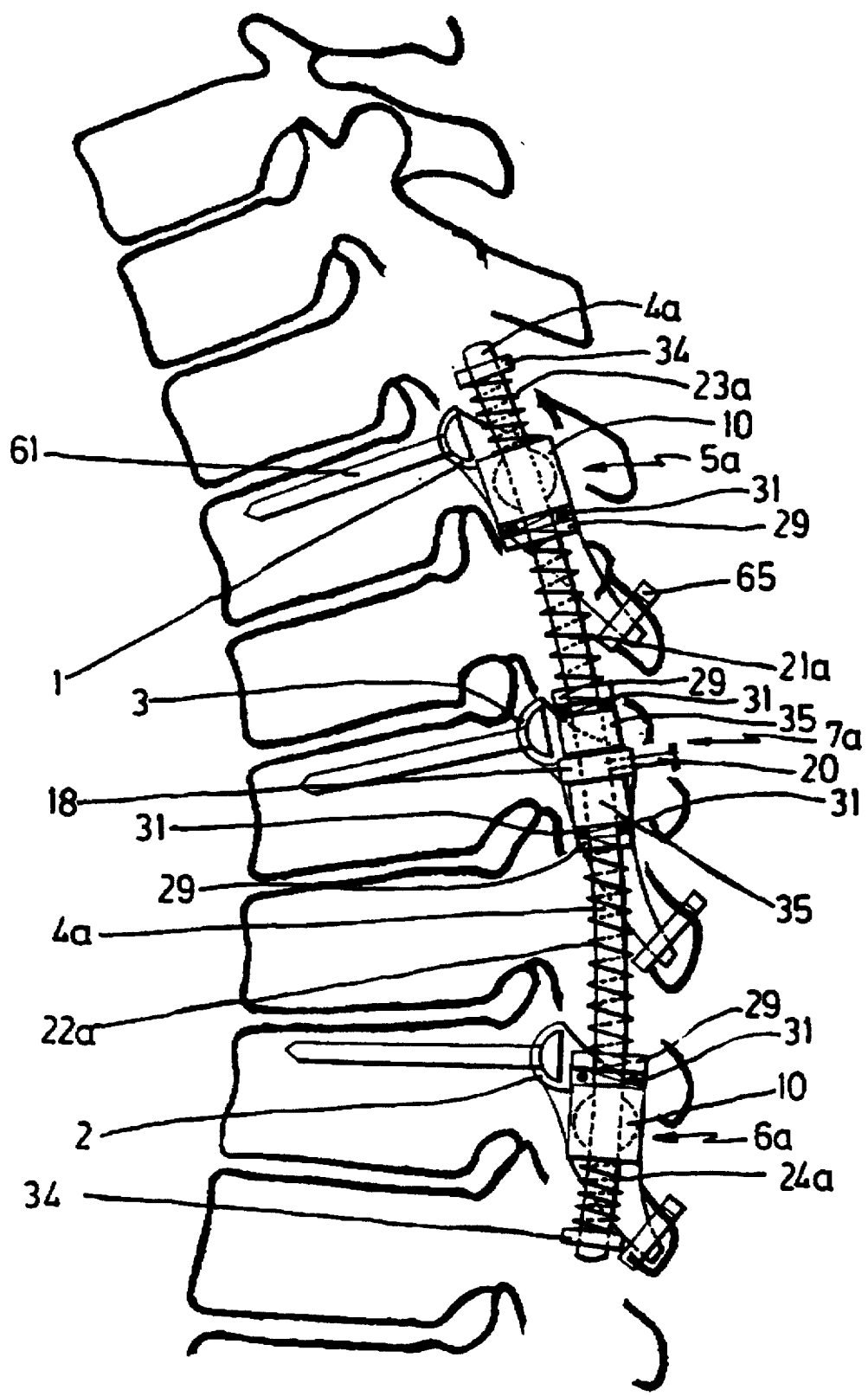
FIG. 2 is a diagrammatic side view of a second embodiment of an orthosis according to the invention, more particularly designed for the treatment of scoliosis.

FIG. 2 shows a side view of a variant embodiment of the orthosis described above. As can be seen, the curvature of the rod 4a makes it possible to reestablish and maintain the kyphosis. In this variant embodiment, the cylinder 18 of the middle coupling means 7a is provided with an electronic micromotor 35 for adjustment on each side. The two springs 21a, 22a interposed between the anchoring components on each side of the middle cylinder 18 are provided with an adjusting and torsion-locking end ring 29. In this way, this torsion of the springs participates in the derotation of the vertebrae. It should be noted that this derotation is also obtained through the elastic curvature of the rod 4a itself and by the fact that it is fitted with its plane of curvature when idle being inclined with respect to a sagittal plane.

Figure 8:
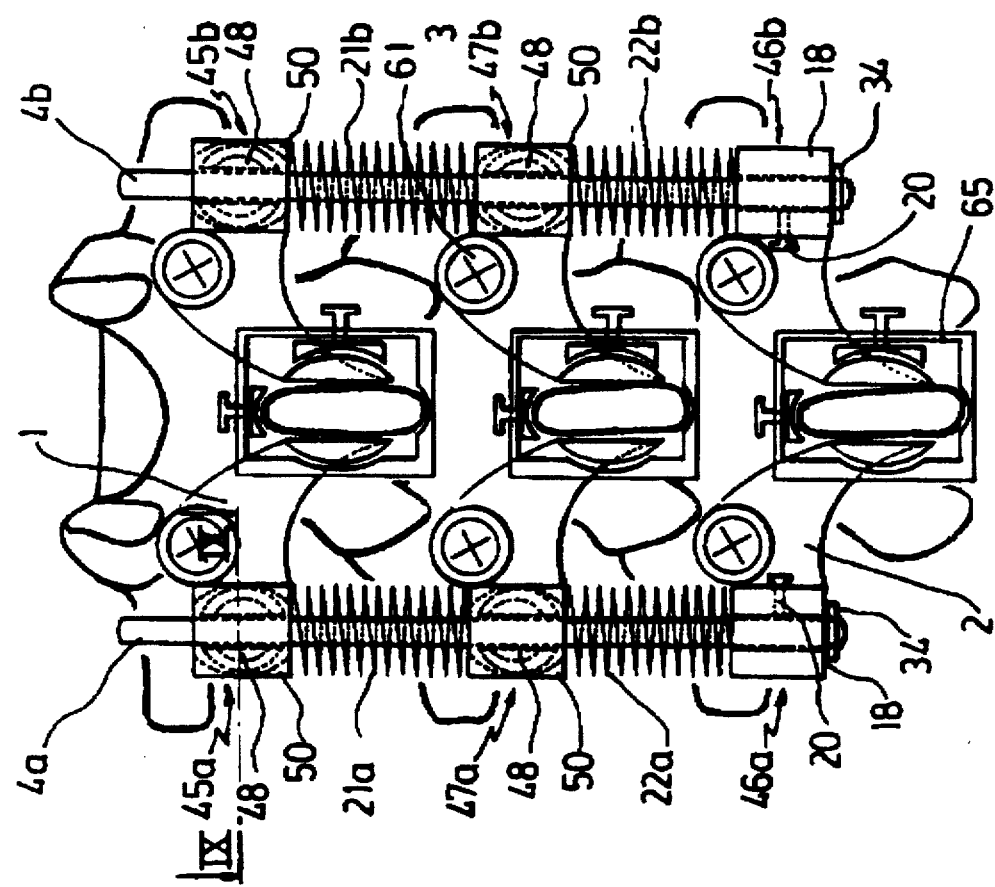
FIG. 8 is a diagrammatic posterior view of a third embodiment of an orthosis according to the invention, more particularly designed for treating a degenerative lumbar instability.

FIG. 8 shows an embodiment of an orthosis according to the invention more particularly designed for treating a degenerative lumbar instability. Unlike the orthosis described above, which makes it possible to fit an appliance to a length of spinal column corresponding to five vertebrae, this short lumbar orthosis extends over a more limited number of vertebrae, notably three vertebrae in the example shown.

This short orthosis also includes components 1, 2, 3 for anchoring on three vertebrae, one or two posterior lateral rods 4a, 4b, and springs 21a, 22a, 21b, 22b, each of them being interposed between the components 1, 3 or 3, 2 for anchoring to two different vertebrae. Essentially, the function of a lumbar orthosis of this type is not to correct a deformation, but to correct the magnitude of the forces exerted between vertebrae and reducing the forces to which the vertebrae are subjected because of the degenerative instability. After the fitting of the orthosis, ie in the so-called corrected position of the vertebrae, the springs and the elasticity of the rods enable these forces exerted between vertebrae to be modified by reducing the forces applied to the spinal column without suppressing the natural physiological mobility. Consequently, the springs 21a, 21b, 22a, 22b are all compression springs acting in the direction of separation of the vertebrae with respect to each other in order to take the load off the posterior vertebral joints. The rods 4a, 4b are curved in the direction of the lordosis and enable the relative positions of the vertebrae to be maintained, and in particular the separation of the vertebral bodies, which reduces the forces applied to the anterior discoligamentary system. The springs bear directly on the anchoring components since no correction generally needs to be effected in the direction of rotation about the vertical axis.

The orthosis shown in FIG. 8 also differs from the ortheses shown in FIGS. 1 and 2 because of the means 45a, 45b, 46a, 46b, 47a, 47b of coupling the rods 4a, 4b to the anchoring components 1, 2, 3. This is because these coupling means do not have the same degrees of freedom. More precisely, to maintain the separation between the vertebral bodies more effectively, the degree of freedom in rotation about an axis perpendicular to the sagittal plane is eliminated at all the vertebrae. Thus the means 45a, 45b, 47a, 47b for coupling the rods 4a, 4b to the top 1 and middle 3 anchoring components allow relative movements of the rods 4a, 4b with respect to these anchoring components 1, 3 in longitudinal translation along a vertical axis, in relative rotation about an axis perpendicular to a frontal plane, and in inherent rotation of the rod about a vertical axis, but prevent any relative rotation about an axis perpendicular to a sagittal plane. To achieve this, the sphere 8 of the orthosis described previously is replaced by a sphere 48 provided with an annular circumferential projection 52, and the housing 49 for receiving the sphere 48 has an annular groove 53 in which the projection 52 on the sphere is engaged. The projection 52 and the groove 53 lie in a frontal plane so as to allow rotation about an axis perpendicular to the frontal plane while preventing rotations about an axis perpendicular to the sagittal plane. In a variant, these coupling means could also be produced in the form of a cylinder with a horizontal axis and provided with a radial drilling for the rod engaged in a cylindrical housing with an anteroposterior horizontal axis in the cylinder 50 to pass through. The member 48 mounted so as to rotate with respect to the cylinder 50 (ie the sphere 48 or the horizontal-axis cylinder) has a bore 51 with a vertical axis for the rod 4a, 4b to pass through. Rotations about an axis perpendicular to the sagittal plane are not possible at the coupling components but are made possible at the holding and elastic return components by the flexibility of the rods and springs, so as to allow the spinal column to make physiological bending and extension movements in the sagittal plane.

The means 46a, 46b for coupling the rods 4a, 4b to the bottom anchoring components 2 are rigid connection means locking the rod in all directions, ie are identical to the means 7a, 7b for coupling the rods to the middle anchoring components described with reference to FIGS. 1 and 2. These coupling means 46a, 46b therefore include a cylinder 18 provided with a bore 19 and at least one transverse locking screw 20. A nut 34 is fixed to the bottom end 26a, 26b of each rod 4a, 4b. On the other hand, the top free ends 25a, 25b of the rods 4a, 4b are left free without a nut or spring.

Figure 9:
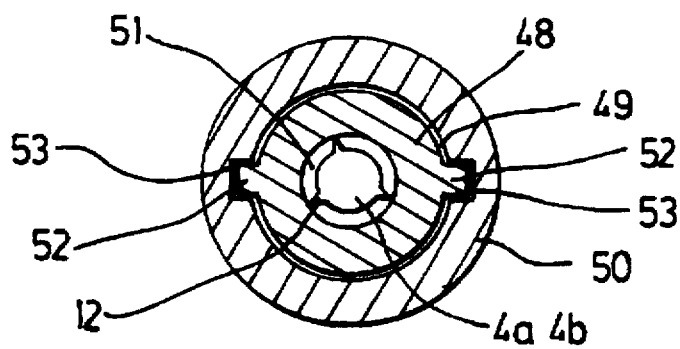
FIG. 9 is a diagrammatic view in detailed cross section along the line IX—IX in FIG. 8.
Figure 10:
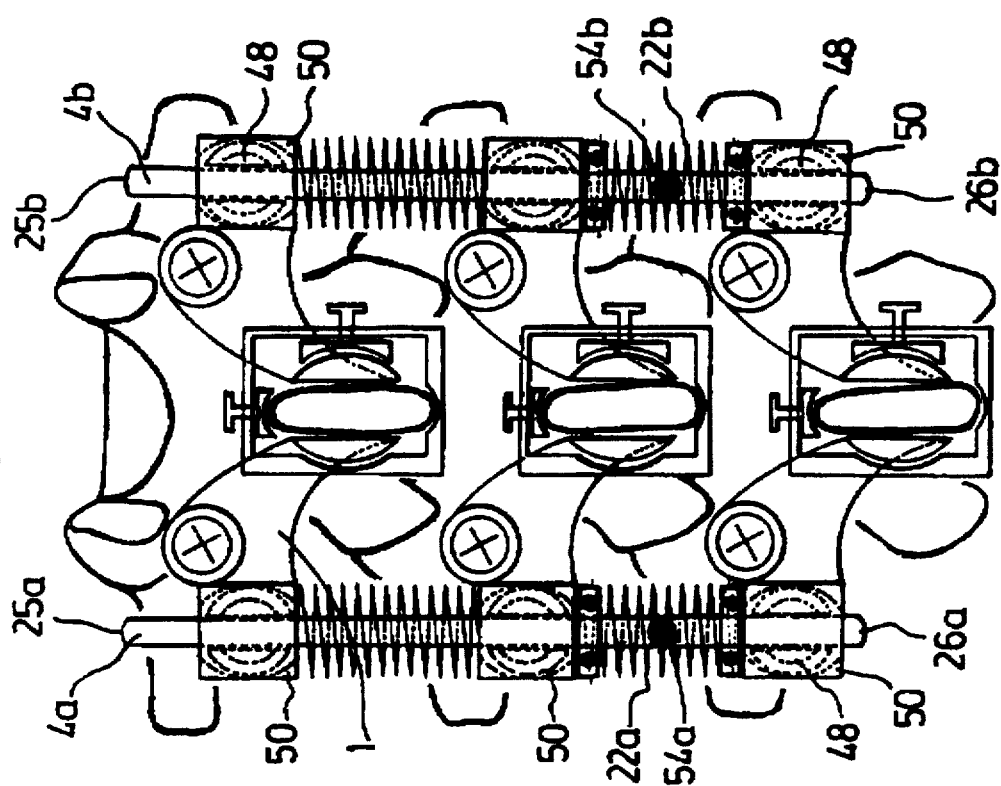
FIG. 10 is a posterior diagrammatic view of a fourth embodiment of an orthosis according to the invention, more particularly designed for treating a degenerative lumbar instability.

FIG. 10 shows a variant embodiment of the short lumbar orthosis according to the invention. In this variant, all the coupling means have the same degrees of freedom and are identical to the coupling means 45a, 45b, 47a, 47b in the embodiment shown in FIGS. 8 and 9. The rods 4a, 4b are held in position with respect to the coupling means 45a, 45b, 46a, 46b, 47a, 47b and opposite the corresponding vertebrae by a welding 54a, 54b rigidly connecting a coil of the springs 22a, 22b to the outer surface of the rods 4a, 4b. In this embodiment, the springs 22a, 22b also have at each end a ring 29 locked by screws 32 with respect to the cylinders 50 of the corresponding coupling means 46a, 46b, 47a, 47b enabling these springs 22a, 22b to be locked with respect to rotation about the vertical axis. The rod 4a, 4b is therefore held with respect to rotation about the vertical axis by the springs 22a, 22b, in the desired lordosis position.

The embodiments shown in FIGS. 8 and 10 can also include, if necessary, means—in particular micromotors 35 and/or manual tensioning devices 36—of adjusting the elastic return force exerted by the springs 21a, 21b, 22a, 22b.

In addition, and in all the embodiments of the invention, the orthosis may include means of adjusting the elastic return forces exerted by the elastic return means produced in the form of at least part of the holding means and/or elastic return means made from a shape-memory metal alloy. For example, all or some of the rods 4a, 4b and/or all or some of the springs may be made from a shape-memory metal alloy. Consequently, after implantation, it will be possible to modify the elastic return forces exerted by transcutaneous heating of this part made from a shape-memory alloy, for example by means of microwaves.

The anchoring components 1, 2, 3 include (FIG. 15) at least one plate 55 having an anterior convex face coming to bear in contact with the vertebral lamina 57 on at least one side of the spinous process 58. The cylinders 10, 18, 50 of the coupling means are carried by a plate 55 opposite the transverse end of the lamina 57 near the transverse process 59. Each plate 55 is fixed to a vertebra on at least two different places. For example, each plate 55 is fixed to the corresponding vertebra by an intrapedicular screw 61 and/or clamping hooks 71 on the transverse process 59 and/or a clamping collar 65 on the spinous process 58.

The anchoring components may include two plates 55a, 55b, one oh each side of the spinous process, even when the orthosis has only a single rod on a single side of the spinous process (FIG. 15). As a variant, a single plate 55 may be provided. In all cases, the anchoring components according to the invention are in accordance with the discoligamentary and articular structures of the vertebrae, the integrity of which will enable the physiological spinal movements to be preserved. In particular, the anchoring components according to the invention enable the movements allowed by the dynamic orthosis to be preserved. In addition, if this orthosis is then removed, for example when the patient ceases to grow, natural physiological movements are possible.

The orthosis according to the invention can be produced at least in part using a metal alloy (stainless steel, titanium, etc) and/or a composite material.

Figure 17:
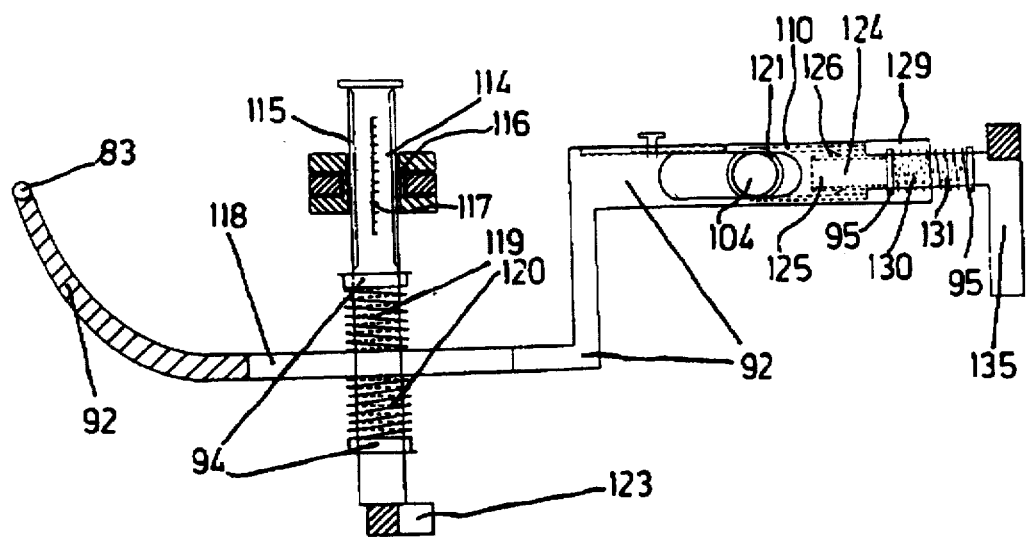
FIG. 17 is a diagrammatic view in cross section along the line XVII—XVII in FIG. 16.
Figure 16:
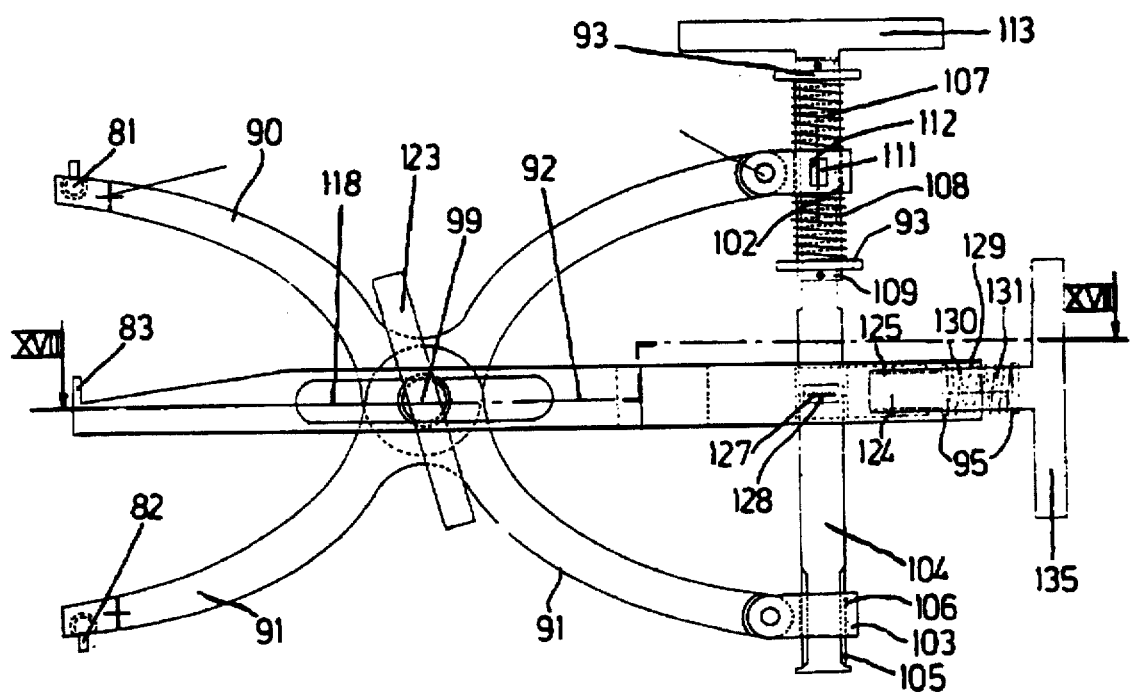
FIG. 16 is a diagrammatic posterior view of a clamp forming part of operative instrumentation according to the invention.

FIGS. 16 and 17 show a clamp forming part of operative instrumentation for the fitting of a spinal orthosis implanted according to the invention. This clamp has three active ends 81, 82, 83 designed to cooperate respectively with the components 1, 2, 3 for anchoring the vertebrae.

Each of the active ends 81, 82, 83 of the clamp is formed by a stud designed to be engaged in a drilling 78 with a vertical axis made near the coupling means of the anchoring components 1, 2, 3. Each stud 81, 82, 83, which can be orientated downwards or upwards (FIG. 16), can act in compression or traction as required. Thus each plate 55 on the anchoring components has a drilling 78 made through a horizontal extension of the plate 55, which supports a cylinder 10, 18 or 50 for coupling a rod 4a, 4b. The drilling 78 is preferably made in the front and lateral side of the cylinder 10, 18, 50.

According to the invention, the clamp also includes dynamometric means 93, 94, 95 for measuring the forces exerted on the end studs 81, 82, 83 to maintain their relative positions. Also, the clamp includes means 112, 117, 127 for measuring the movements of the end studs 81, 82, 83 during changes in their relative positions.

Each clamp consists of three articulated arms 90, 91, 92 carrying the studs 81, 82, 83 at their free end. More precisely, the clamp has a top arm 90 carrying the top end stud 81, a bottom arm 91 carrying the bottom end stud 82, and a middle arm 92 carrying the middle end stud 83. The two top and bottom arms 90, 91 are articulated on each other about a horizontal axis 99 orthogonal to the direction passing through the two studs 81, 82. The arms 90, 91, 92 are articulated with respect to each other and controlled in their relative movements by three control rods 104, 114, 124 equipped with handles 113, 123, 135. A vertical control rod 104 has a thread 105 cooperating with an internal screw thread 106 on an end 103 of the bottom arm 91 opposite the stud 82. The end 102 of the top arm 90 opposite the stud 81 is in the form of a sleeve sliding about a cylinder 109 fixed to the vertical control rod but whose position in translation with respect to the rod 104 can be adjusted. This sleeve 102 is trapped between two compression springs 107, 108 surrounding the rod 104 and bearing, at their opposite ends, on dynamometric sensors 93. The sleeve 102 also has an aperture 111 enabling a graduated scale 112 on the rod 104 to be read. When the handle 113 is turned, the end studs 81, 82 are moved away from or towards each other. If the studs 81, 82 are not subjected to any forces in the vertical direction, the top sleeve 102 remains half way between the two sensors 93, the springs 107, 108 not being actuated. If, on the other hand, a force is necessary to move the studs 81, 82, one of the springs 107, 108 is actuated in compression to balance this force and enable the position to be modified. The dynamometric sensors 93 then give an electrical signal which is proportional to this force.

The middle arm 92 is articulated on the assembly thus formed by the top 90 and bottom 91 arms. A sagittal control rod 114 extends along the articulation axis 99 of the top and bottom arms 90, 91 in the sagittal direction. This rod 114 has, at its end, a thread 115 engaged in an internal screw thread 116 in one of the arms 90, 91. The rod 114 also carries a graduated scale 117 enabling its position with respect to the arms 90, 91 to be determined. The middle arm 92 has an oblong aperture 118, through which the control rod 114 passes. This oblong aperture 118 extends in a direction orthogonal to the vertical direction passing through the top and bottom end studs 81, 82, and to the horizontal articulation axis 99 of the two top and bottom arms 90, 91. Thus a movement of the middle arm 92 with respect to the articulation axis 99 and in this direction is possible. The oblong aperture 118 in the middle arm 92 is engaged about the control rod 114 trapped between two springs 119, 120, the opposite ends of which bear on dynamometric sensors 94. These dynamometric sensors 94 provide a measurement of the forces exerted on the stud 83 in the horizontal sagittal direction. By turning the handle 123, the position of the stud 83 is therefore modified in the horizontal sagittal direction with respect to the frontal plane containing the top and bottom studs 81, 82.

The end 129 of the middle arm 92 opposite the end stud 83 is associated with a frontal control rod 124 which enables the movements of this middle arm to be controlled in the horizontal frontal direction perpendicular to the vertical direction passing through the top and bottom end studs 81, 82 and to the articulation axis 99 of the two top and bottom arms 90, 91. This frontal control rod 124 has a threaded end 125 engaged in an internal screw thread 126 in a bearing 110 comprising a cylinder 121 surrounding the vertical control rod 104. The cylinder 121 carries a graduated scale 127 which can be seen through an aperture 128 in the middle arm 92. The end 129 of the middle arm 92 opposite the stud 83 slides about the frontal control rod 124 and is trapped between two springs 130, 131, the opposite ends of which bear on dynamometric sensors 95. Movement of the middle arm 92 in the frontal direction is allowed by virtue of the oblong aperture 118 and the other one around the vertical control rod 104. By turning the handle 135, the position of the middle stud 83 is thus modified in the frontal direction with respect to the sagittal plane containing the top and bottom studs 81, 82. The sensors 95 provide a measurement of the forces necessary for this movement.

In the procedure for fitting an orthosis according to the invention, the vertebrae intended to receive the anchoring components 1, 2, 3 are exposed, the anchoring components 1, 2, 3 are positioned and fixed onto each vertebra in question and bilaterally (FIG. 11), at least one operative clamp is connected to the anchoring components 1, 2, 3 for each vertebra to be moved for the required correction, and notably a clamp for each rod 4a or 4b which is to be fitted (FIG. 12), the handles 113, 123, 135 of each clamp are operated in order to place the vertebrae in the corrected position to reduce the deformation and/or exert the desired static forces (FIG. 13), the necessary holding forces applied to the anchoring components 1, 2, 3 for each vertebra are measured by means of the various dynamometric sensors 93, 94, 95 in order to maintain the said corrected position, the characteristics of the holding means and elastic return means of the orthosis for generating the elastic return forces similar to the measured holding forces are determined, the holding and/or elastic return means (FIG. 14) are positioned, ie the rods 4a, 4b and springs are positioned by connecting them by means of the various means of coupling to the anchoring components 1, 2, 3, the operative instrumentation is removed (FIG. 1), and the surgical implantation procedure is completed.

Figure 12:
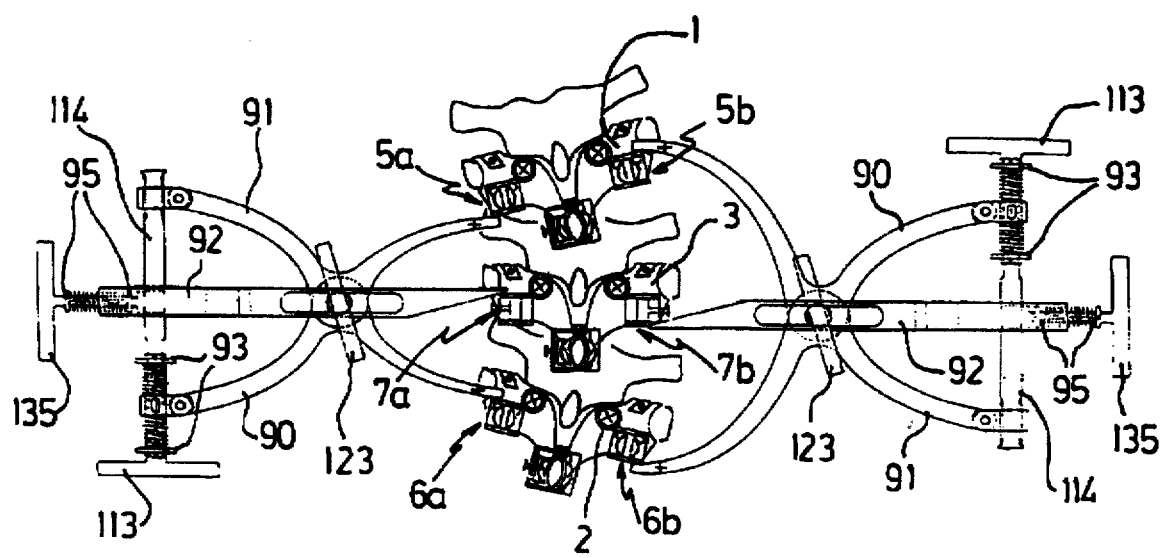
FIG. 12 is a posterior diagrammatic view illustrating a second stage of fitting the orthosis in FIG. 1.
Figure 14:
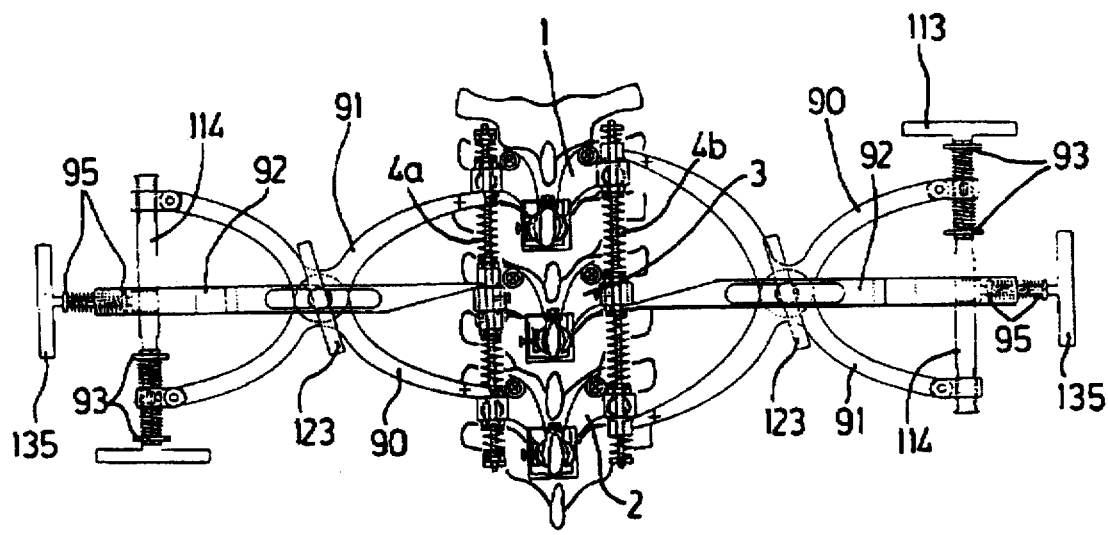
FIG. 14 is a diagrammatic posterior view illustrating a fourth stage of fitting the orthosis in FIG. 1.
Figure 13:
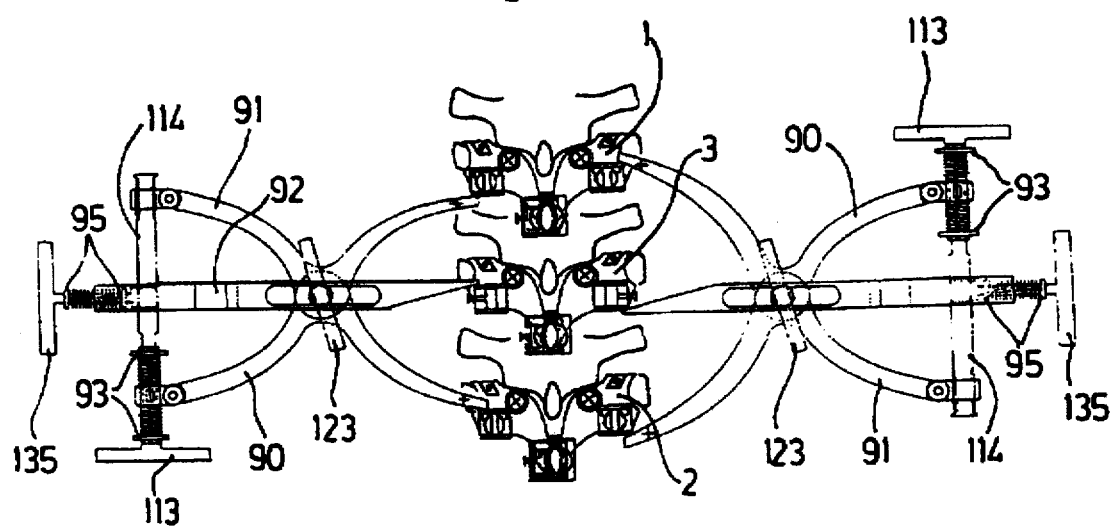
FIG. 13 is a diagrammatic posterior view illustrating a third stage of fitting the orthosis in FIG. 1.

In FIGS. 12 to 14, the clamp placed to the right of the spinous processes is similar to the one described and shown in FIGS. 16 and 17, and the clamp placed to the left is reversed, the said top arm 90 being associated with the bottom anchoring components 2 and the said bottom arm 91 being associated with the top anchoring components 1. The dimensions and shape of the arms 90, 91 used are chosen in accordance with the distance between the corresponding vertebrae.

According to the invention, the deformation and/or the forces are therefore fully corrected, by means of the operative clamps, before connecting the holding and/or elastic return means (rods and springs), in contrast with the known osteosynthesis devices, with which the correction is effected by or with Components which rigidify the spine.

The holding forces are measured by means of dynamometric sensors 93, 94, 95 fixed to the operative instrumentation, ie along three orthogonal translational axes of the end studs 81, 82, 83, namely a vertical axis (vertical control rod 104), a sagittal axis (sagittal control rod 114), and a frontal axis (frontal control rod 124).

The various characteristics and dimensions of the holding and/or elastic return means are determined, at least approximately, by computations made by a programmed data processing device for this purpose using the values of the holding forces measured by the various dynamometric sensors. The required efficacy of the holding and/or elastic return means of the orthosis is verified before the removal of the clamps by reading the overcoming of the static forces registered by the dynamometers 93, 94, 95. The holding and elastic return means are then and if necessary entirely or partly adjusted or changed.

Using the means of adjusting the elastic return means of the orthosis, after removing the operative instrumentation, the maintenance of the corrected position and/or of the desired value of the static forces between vertebrae can be checked, and any adjustments necessary are then made before completing the surgery or after the surgery when the patient is awake.

Figure 18:
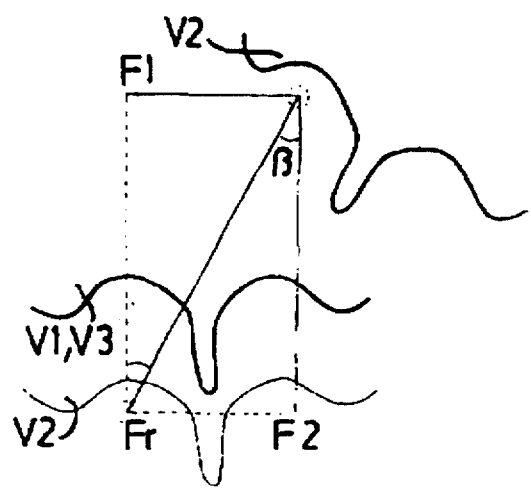
FIG. 18 is a theoretical cross-sectional diagram in a horizontal plane enabling the characteristics of a holding and elastic return rod of an orthosis according to the invention to be determined.
Figure 19:
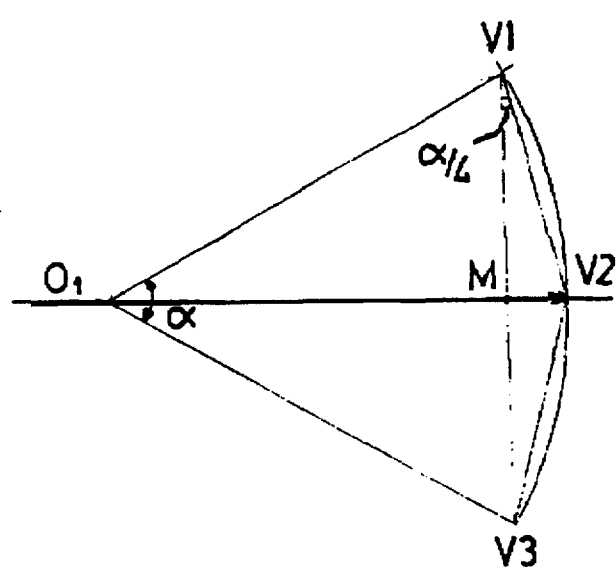
FIG. 19 is a theoretical cross-sectional diagram in a sagittal plane enabling the characteristics of a holding and elastic return rod of an orthosis according to the invention to be determined.

FIGS. 18 and 19 illustrate a diagram enabling the main characteristics and the orientation of each rod $4a$, $4b$ of an orthosis according to the invention to be determined.

The rod $4a$, $4b$ is fitted by orientating its curvature plane by an angle $\beta$ (FIG. 18) with respect to the sagittal plane of the spinal column in the corrected position. This angle $\beta$ makes it possible to determine the positioning of the middle vertebra V2 in the sagittal plane of the top and bottom vertebrae V1 and V3. If F1 and F2 are the measured values (given by the sensors 95, 94) of the holding forces in the frontal direction and sagittal direction respectively, this gives:

$$\tan\beta = F1/F2$$

From this value of $\beta$ obtained by calculation, a clamp is fixed to the rod, before it is fitted, in the plane of its curvature, and this clamp is orientated with respect to the sagittal plane after engaging the rod in the coupling means of the orthosis, using a protractor placed in the horizontal plane of the patient. The screws 20 for locking the rod with respect to the cylinder 18 are then tightened in order to lock it to the anchoring components 3 for the middle vertebra with respect to rotation about the vertical direction.

The sagittal movement MV2 which must then be given to the middle vertebra by the sagittal control rod 114 to re-establish the kyphosis is illustrated in FIG. 19. If a is the Cobb angle of the kyphosis which should be provided between the end vertebrae V1 and V3, this gives:

$$MV2 = \tan(\alpha/4) \times \frac{V1V3}{2}$$

where V1V3 is the vertical distance separating the two top and bottom vertebrae.

The calculations are the same for the concavity and the convexity.

The initial curvature of each rod $4a$, $4b$ corresponds to the desired final curvature given by the angle $\alpha$ as modified by the deformation of the rod due to the elastic holding forces which it must exert. The resulting elastic force FR which the rod must exert is:

$$FR = \sqrt{F1^2 + F2^2}$$

The length of the rod depends on the distance between the vertebrae fitted with the device, and its diameter is chosen as a function of the curvature and the material to obtain the force FR with sufficient residual flexibility to allow physiological spinal movements.

The compression and extension springs are sized conventionally, essentially using the value of the vertical holding forces supplied by the sensors 93 of the vertical control rod 104.

The coil springs operating in torsion are tensioned in the opposite direction to the winding of the coils, ie reducing the diameter of the spring. The top springs $21a$, $21b$ are both wound in the same direction, and in the opposite direction to the bottom springs $22a$, $22b$. The coils of the springs are tensioned so as to achieve the derotation of the vertebrae in the desired direction.

The orthosis according to the invention may be the subject of numerous variants, notably in accordance with the deformation or instability in the patient to be corrected and the surgical conditions encountered. In particular, the orthosis may include solely holding and elastic return rods, or solely holding and elastic return springs. The springs may also be leaf or other springs. Covers for the springs protecting against fibrotic invasion may be provided.

Besides, the orthesis according to the invention may be used wih any part of the spinal column and is not restricted to the correction of dorsal kyphoscoliosis and degenerative lumbar instabilities as illustrated by the examples. In particular the orthesis according to the invention is appliable with minor amendments on a part of cervical column.

I claim:

1. An implanted dynamic vertebral orthosis for adjusting the relative positions of spinal vertebrae with respect to a vertical axis comprising anchoring members for securing to the vertebrae and holding means connected to the anchoring members, said holding means including at least one curved holding rod which is flexible and elastic in bending and connected to said anchoring members for anchoring at least two different vertebrae, and coupling means for connecting said holding rod to said anchoring members, wherein said coupling means comprises a first coupling member preventing all relative horizontal translational sliding movement of the vertebrae, while permitting relative longitudinal translational sliding movement along said vertical axis and relative rotational movement about said vertical axis of said holding means having elastic return means capable of exerting elastic return forces having predetermined orientation and magnitude between said anchoring members, for holding the vertebrae in a predetermined corrected position against natural deforming forces for reducing the overall forces exerted on the vertebrae.

2. An orthosis as in claim 1, wherein said coupling means further includes a second coupling member for rigidly connecting said holding rod to said anchoring members and preventing all relative lateral movements of the vertebrae with respect to said vertical axis while permitting said relative longitudinal translational sliding movement and said relative rotational movement about said vertical axis.

3. An orthosis as in claim 1, and wherein said coupling means permits relative rotation of said holding rod about an axis perpendicular to a frontal plane of said orthosis.

4. An orthosis as in claim 3, and wherein said coupling means permits relative rotation of said holding rod about an axis perpendicular to a sagittal plane of said orthosis.

5. An orthosis as in claim 1, and wherein said holding rods have a shape when connected to said anchoring members which is elastically different from their shape when not so connected, so as to exert elastic return forces when the vertebrae are in the corrected position.

6. An orthosis as in claim 5, and wherein said coupling means permits rotation of said holding rod about the longitudinal axis of said holding rod.

7. An orthosis as in claim 1, and wherein said coupling means includes a cylindrical bore, said holding rod passing slidably through said bore.

8. An orthosis as in claim 7, and wherein said bore is formed in one of said coupling members, said one of said coupling members being rotatably mounted with respect to said anchoring members about an axis perpendicular to the frontal plane of of said orthosis.

9. An orthosis as in claim 8, and wherein said coupling member is mounted so as to be rotatable about an axis perpendicular to the sagittal plane of said orthosis.

10. An orthosis as in claim 8, and wherein said coupling member is a sphere having a cylindrical bore and a spherical housing on said anchoring member.

11. An orthosis as in claim 1, and wherein said elastic return means includes at least one spring.

12. An orthosis as in claim 1, and including on one side of said vertical axis a holding rod and at least one compression spring surrounding said holding rod.

13. An orthosis as in claim 1, and wherein said elastic return means comprises at least one torsion spring having coils surrounding said holding rod and locked to said anchoring member for imparting a torsional force to said holding rod.

14. An orthosis as in claim 1, and including means for adjusting the magnitude of said elastic return forces exerted by said elastic return means.

15. An orthosis as in claim 14, and wherein said adjusting means includes means for varying the elastic elongation of the elastic return means.

16. An orthosis as in claim 14, and wherein said adjusting means includes a stop for the elastic return means and at least one device for adjusting the position of said stop.

17. An orthosis as in claim 14, and including means for percutaneous control of said adjusting means after implantation of the orthosis.

18. An orthosis as in claim 14, and wherein said elastic return means is formed from a shape-memory metal alloy.

19. A process for effecting and maintaining a correction of the relative positions of spinal vertebrae while preserving at least in part the natural physiological mobility of the vertebrae, and implanting a dynamic spinal orthosis by fixing anchoring members to the vertebrae, and connecting holding means to the anchoring members, and including the steps of exposing the vertebrae to be corrected, fitting and securing the anchoring members to the vertebrae to be corrected, connecting an operative instrumentation to the anchoring members, applying holding forces along three orthogonal axes to the anchoring members for each vertebra for placing the vertebrae in a corrected position, and measuring the holding forces necessary along said axes for each vertebra for maintaining the vertebra in the corrected position, determining the characteristics of the holding means required for generating elastic return forces as a function of the measured holding forces, adjusting the orthosis as a function of the characteristics determined, connecting the holding means to the anchoring members, and thereby imparting the elastic return forces to each vertebra, removing the operative instrumentation and closing the surgical site.

20. A process as in claim 19, and including determining said characteristics by means of dynamometric sensors on the operative instrumentation.

21. A process as in claim 19, and including adjusting the holding means for generating elastic return forces for maintaining the corrected position of the vertebrae.

22. Implanted dynamic vertebral orthosis comprising anchoring members for securing to the vertebrae and holding means associated with the anchoring components, wherein the holding means include at least one curved holding rod which is flexible and elastic in bending connected with components for anchoring at least two different vertebrae, wherein each holding rod is connected to the anchoring components by first coupling means preventing all relative sliding movement in horizontal translation with respect to the vertebrae, wherein each holding rod is connected with the anchoring components for at least one vertebra by second coupling means allowing sliding in relative longitudinal translation along a vertical axis, wherein each holding rod is connected with the anchoring components for at least one vertebra by third coupling means allowing relative rotation about a vertical axis, wherein each holding rod is connected with the anchoring components for at least one vertebra by fourth coupling means allowing relative rotation about an horizontal axis, and wherein the holding means is capable of exerting elastic return forces having orientation and magnitude for holding the vertebrae in the corrected position against the natural deforming forces.

23. A dynamic, implantable vertebral orthosis for adjusting the relative positions of spinal vertebrae comprising anchoring members securable to the vertebrae and holding means associated with the anchoring members, said holding means including at least one curved holding rod which is flexible and elastic upon bending and connected to said anchoring members for attachment to at least two different vertebrae, and coupling means for connecting said holding rod to said anchoring members, said coupling means preventing all relative horizontal translational sliding movement of the vertebrae, said coupling means further permitting relative longitudinal translational sliding movement along a vertical axis and relative rotational movement of the vertebrae about a vertical axis, said holding means having elastic return means capable of exerting elastic return forces having adjustable orientation and magnitude for maintaining the vertebrae in a corrected position against natural deforming forces, or so as to reduce the overall forces exerted on the vertebrae while preserving the mobility and allowing physiological movements of the vertebrae.

24. A vertebral orthosis as in claim 23 and wherein said coupling means comprises a spherical member having a cylindrical bore therethrough, said holding rod being slidable in and passing through said bore.

25. A vertebral orthosis as in claim 24 and including a spherical housing for said spherical member whereby said spherical member is rotatable in said spherical housing.

26. A vertebral orthosis as in claim 25 and including means for adjusting the position of said rod in said spherical member.

\* \* \* \* \*